United States Patent
Schoepgens et al.

(10) Patent No.: US 10,653,598 B2
(45) Date of Patent: *May 19, 2020

(54) DECOLORING OF DYED KERATIN FIBERS

(71) Applicant: Henkel AG & Co. KGaA, Duesseldorf (DE)

(72) Inventors: Juergen Schoepgens, Schwalmtal (DE); Burkhard Mueller, Duesseldorf (DE)

(73) Assignee: Henkel AG & Co. KGaA (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/348,428

(22) Filed: Nov. 10, 2016

(65) Prior Publication Data

US 2017/0128334 A1 May 11, 2017

(30) Foreign Application Priority Data

Nov. 11, 2015 (DE) .......................... 10 2015 222 214

(51) Int. Cl.

| | | |
|---|---|---|
| *A61K 8/362* | (2006.01) | |
| *A61Q 5/12* | (2006.01) | |
| *A61K 8/22* | (2006.01) | |
| *A61K 8/23* | (2006.01) | |
| *A61Q 5/08* | (2006.01) | |
| *A61K 8/46* | (2006.01) | |
| *A61K 8/34* | (2006.01) | |
| *A61K 8/55* | (2006.01) | |
| *A61K 8/41* | (2006.01) | |
| *A61K 8/44* | (2006.01) | |
| *A61K 8/365* | (2006.01) | |
| *A61Q 5/10* | (2006.01) | |

(52) U.S. Cl.
CPC ................ *A61K 8/362* (2013.01); *A61K 8/22* (2013.01); *A61K 8/23* (2013.01); *A61K 8/342* (2013.01); *A61K 8/365* (2013.01); *A61K 8/41* (2013.01); *A61K 8/411* (2013.01); *A61K 8/415* (2013.01); *A61K 8/447* (2013.01); *A61K 8/46* (2013.01); *A61K 8/463* (2013.01); *A61K 8/55* (2013.01); *A61Q 5/08* (2013.01); *A61Q 5/10* (2013.01); *A61Q 5/12* (2013.01); *A61K 2800/88* (2013.01); *A61K 2800/882* (2013.01)

(58) Field of Classification Search
None
See application file for complete search history.

(56) References Cited

U.S. PATENT DOCUMENTS

| | | |
|---|---|---|
| 3,547,828 A | 12/1970 | Mansfield et al. |
| 3,839,318 A | 10/1974 | Mansfield et al. |
| 5,254,336 A * | 10/1993 | Hoshowski ............ A61K 8/365 132/202 |
| 5,374,716 A | 12/1994 | Biermann et al. |
| 6,730,132 B1 | 5/2004 | Beckmann et al. |
| 2013/0184195 A1 | 7/2013 | Sadlowski et al. |

FOREIGN PATENT DOCUMENTS

| | | |
|---|---|---|
| DE | 3929973 A1 | 3/1991 |
| DE | 19710154 A1 | 9/1998 |
| EP | 1300136 A2 | 4/2003 |
| EP | 2809401 B1 | 3/2017 |
| JP | 2004149484 A | 5/2004 |
| JP | 2004149485 A | 5/2004 |
| WO | 2006106390 A2 | 12/2006 |
| WO | 2008/055756 A1 | 5/2008 |
| WO | 2012069599 A2 | 5/2012 |
| WO | WO-2013017862 A2 * | 2/2013 ............... A61K 8/22 |

OTHER PUBLICATIONS

Ehlers et al. English translation of EP 1300136 A2 (Year: 2003).*
PCT International Search Report (PCT/EP2015/075799) dated Feb. 12, 2016.
GB131618976.3.3 Patents Act 1977/Examination Report Under Section 18(3) dated Feb. 27, 2019 40 pages.
FR16660661 Preliminary Search Report dated Feb. 10, 2019 10 pages.
DE 10 2015222214.4 Examination Report dated Jan. 22, 2020 10 pages.

* cited by examiner

*Primary Examiner* — Nicole P Babson
(74) *Attorney, Agent, or Firm* — James J. Cummings

(57) ABSTRACT

A multi-component packaging unit (kit of parts) for reductively decoloring dyed keratin fibers, includes
(I) a container (A) containing a cosmetic agent (a) and
(II) a container (B) containing a cosmetic agent (b) and
(III) a container (C) containing an aqueous, cosmetic agent (c)
produced separately from each other, wherein
  agent (a) in container (A) includes a reductant (a1) as defined herein and
  agent (c) in container (C) includes
    (c1) one or more compounds of formula (I),

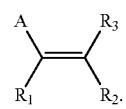

(I)

A method for reductively decoloring dyed keratin fibers includes using the multi-component packaging unit.

20 Claims, No Drawings

DECOLORING OF DYED KERATIN FIBERS

FIELD OF THE INVENTION

The present invention generally relates to cosmetics, and more particularly relates to multi-component packaging units (kits of parts) for reductively decoloring dyed keratin fibers, which include three containers (A), (B), and (C), which are produced separately with respect to each other. Container (A) contains a cosmetic agent (a) having at least one selected reductant, container (B) contains a cosmetic agent (b) acting as a carrier, and container (C) contains an aqueous cosmetic agent (c), which includes at least one unsaturated acid and/or a physiologically acceptable salt thereof.

These three agents (a), (b), and (c) should be used in methods for reductively removing color from dyed keratin fibers, more particularly human hair. A corresponding method is also subject matter of the present application. For the purpose of reductive color removal, agent (a), which includes the reductant, is mixed with cosmetic carrier agent (b), and this application mixture is applied to dyed keratin fibers. After an application time period of 2 to 60 minutes, the decoloring agent can optionally be washed out and the keratin fibers can be dried. Thereafter, the keratin fibers are post-treated with post-treatment agent (c).

BACKGROUND OF THE INVENTION

Preparations for tinting and dyeing hair are an important type of cosmetic agent. They can be used to nuance the natural hair color slightly or more heavily in accordance with the wishes of the particular person, to achieve a completely different hair color, or to cover undesired shades of color, such as shades of gray. Depending on the desired color and/or lastingness of the coloring, typical hair dyeing agents are formulated either on the basis of oxidation dyes or on the basis of direct dyes. Combinations of oxidation dyes and direct dyes are also frequently used to achieve specific nuances.

Dyeing agents based on oxidation dyes lead to brilliant and lasting shades of color. However, they require the use of strong oxidants, such as hydrogen peroxide solutions. Such dyes include oxidation dye intermediates: developer components and coupler components. The developer components form the actual dyes among each other or by coupling with one or more coupler components, under the influence of oxidants or atmospheric oxygen.

Dyeing agents based on direct dyes are often used for temporary coloring. Direct dyes are dye molecules that attach directly to the hair and do not require an oxidative process to form the color. Important representatives of this dye class are, for example, triphenylmethane dyes, azo dyes, anthraquinone dyes, or nitrobenzene dyes, each of which can bear cationic or anionic groups.

In the case of all these dyeing processes, it may happen that the coloring should be completely or partially reversed for various reasons. Partial removal of the coloring is useful, for example, if the dyeing result turns out darker than desired on the fibers. On the other hand, complete removal of the coloring is also desired in some cases. For example, it is conceivable that hair should be dyed or tinted in a certain nuance for a specific occasion and then the original color should be recovered after a few days.

Agents and methods for color removal are already known in the literature. A method for reversing colorings that is well known from the prior art is the oxidative decoloring of the dyed hair, for example by means of a typical bleaching agent. However, in this process, the fibers can be damaged by the use of strong oxidants.

Furthermore, reductive processes for color removal have also already been described. For example, European patent application EP 1300136 A2 discloses a method for treating hair in which the hair is dyed in a first step and reductively decolored in a second step. In this method, the reductive decoloring is performed by applying a formulation containing a dithionite salt and a surfactant. In WO 2008/055756 A2, the reductive decoloring of keratin fibers is performed by means of a mixture of a reductant and an absorbent.

If reductive decoloring agents are used, the decoloring occurs by the reduction of the dyes present on the keratin fibers or hair. As a result of the reduction, the dyes are generally converted into the reduced leuco forms thereof. In this process, the double bonds present in the dyes are reduced, the chromophoric system of the dyes is interrupted in this way, and the dye is converted into a colorless form.

A general problem of the reductive decoloring agents known from the prior art is that the dyed keratin fibers can initially be decolored by using the reductant but the color removal is not permanent. Particularly in the case of oxidatively dyed hair, in the case of which the coloring is produced on the hair by means of oxidation dye intermediates of the developer type and of the coupler type, colorings having very good fastness properties in some cases are obtained. When the reductive decoloring agent is applied, these dyes are then reductively converted into colorless compounds—which, however, still remain on the hair due to similarly good fastness properties.

After the reductant has been rinsed off, these reduced forms can then be gradually reoxidized under the influence of atmospheric oxygen. Because of this reoxidation, more or less pronounced recoloring occurs. This recoloring generally does not correspond to the shade of color in which the keratin fibers had been previously dyed, but rather can turn out unattractive in any manner and is therefore desired by the user of the decoloring agent all the less.

Therefore, is desirable to provide a decoloring agent for decoloring dyed keratin fibers that decolors dyed keratin fibers as completely as possible. The decoloring should be long-lasting, and the decolored keratin fibers should not suffer any recoloring, any nuance shift, or any post-darkening under the influence of atmospheric oxygen. The decoloring agent should exhibit good decoloring performance especially on keratin fibers that have been previously dyed by means of oxidative dyeing agents based on oxidation dye intermediates of the developer type and of the coupler type.

Furthermore, other desirable features and characteristics of the present invention will become apparent from the subsequent detailed description of the invention and the appended claims, taken in conjunction with this background of the invention.

BRIEF SUMMARY OF THE INVENTION

A multi-component packaging unit (kit of parts) for reductively decoloring dyed keratin fibers includes (I) a container (A) containing a cosmetic agent (a), and (II) a container (B) containing a cosmetic agent (b), and (III) a container (C) containing an aqueous, cosmetic agent (c), produced separately from each other, wherein agent (a) in container (A) includes (a1) one or more reductants from the group comprising sodium dithionite, zinc dithionite, potassium dithionite, sodium sulfite, sodium hydrogen sulfite, potassium sulfite, potassium hydrogen sulfite, ammonium sulfite, sodium thiosulfate, potassium thiosulfate, ammonium thiosulfate, hydroxymethanesulfinic acid, aminomethanesulfinic acid, formamidine sulfinic acid, [bis(sulfinomethyl)amino]methanesulfinic acid, cysteine, thiolactic acid, thioglycolic acid, ascorbic acid, and/or the physiologically acceptable salts of the aforementioned acids; and agent (c) in container (C) includes (c1) one or more compounds of formula (I),

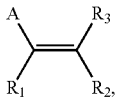

(I)

wherein R1, R2, R3 represent, independently of each other, a hydrogen atom, a —CN group, a —COOM group, a —COOR4 group, a —CONR5R6 group, a phenyl residue, or a C1-C10 alkyl group; M represents a hydrogen atom, an ammonium group $(NH_4)^+$, or an equivalent of a monovalent or multivalent alkali-metal or alkaline-earth-metal cation; R4 represents a $C_1$-$C_6$ alkyl group; R5, R6 represent, independently of each other, a hydrogen atom or a $C_1$-$C_6$ alkyl group; A represents a —COOM group, a —COOR4 group, or a —(CH$_2$)n-COOM group; and n represents an integer from 1 to 10.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

Surprisingly, it has been found that the redarkening occurring after application of the reductive decoloring agent can be effectively suppressed if reductively decolored keratin fibers are treated again after the decoloring with a post-treatment agent that includes at least one specific unsaturated acid of general formula (I).

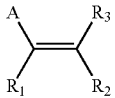

A first subject matter of the present invention is a multi-component packaging unit (kit of parts) for reductively decoloring dyed keratin fibers, which comprises
(I) a container (A) containing a cosmetic agent (a) and
(II) a container (B) containing a cosmetic agent (b) and
(III) a container (C) containing an aqueous, cosmetic agent (c)
produced separately from each other, wherein
agent (a) in container (A) includes
(a1) one or more reductants from the group comprising sodium dithionite, zinc dithionite, potassium dithionite, sodium sulfite, sodium hydrogen sulfite, potassium sulfite, potassium hydrogen sulfite, ammonium sulfite, sodium thiosulfate, potassium thiosulfate, ammonium thiosulfate, hydroxymethanesulfinic acid, aminomethanesulfinic acid, formamidine sulfinic acid, [bis(sulfinomethyl)amino]methanesulfinic acid, cysteine, thiolactic acid, thioglycolic acid, ascorbic acid, and/or the physiologically acceptable salts of the aforementioned acids, and
agent (c) in container (C) includes
(c1) one or more compounds of formula (I),

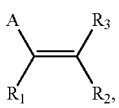

(I)

wherein
R1, R2, R3 represent, independently of each other, a hydrogen atom,
a —CN group, a —COOM group, a —COOR4 group, a —CONR5R6 group, a phenyl residue, or a C1-C10 alkyl group,
M represents a hydrogen atom, an ammonium group $(NH_4)^+$, or an equivalent of a monovalent or multivalent alkali-metal or alkaline-earth-metal cation,
R4 represents a $C_1$-$C_6$ alkyl group,
R5, R6 represent, independently of each other, a hydrogen atom or a $C_1$-$C_6$ alkyl group,
A represents a —COOM group, a —COOR4 group, or a —(CH2)n-COOM group, and
n represents an integer from 1 to 10.

The multi-component packaging unit according to the invention includes containers (A) and (B), which are produced separately from each other and which contain agents (a) and (b), respectively. Agent (a) includes at least one reductant (a1). Agent (b) is a carrier formulation that can be formulated in such a way that the carrier formulation includes water or is water-free. The ready-to-use decoloring agent is produced by mixing the two agents (a) and (b), i.e., by mixing reductant-containing agent (a) with carrier (b).

The multi-component packaging unit according to the invention also comprises a third container (C), which is produced separately and which contains an agent (c). Agent (c) is a post-treatment agent that should be applied to the keratin fibers after the ready-to-use decoloring agent has been applied. By treating the keratin fibers directly after the decoloring, i.e., directly after the application, action, and rinsing out of the ready-to-use decoloring agent, the decoloring can be made more effective and, in particular, the reoxidation leading to post-darkening can be effectively prevented.

Particularly surprisingly, it has been found that the decoloring effect that occurs when the multi-component packaging unit according to the invention is applied is extremely long-lasting and that even the decolored keratin fibers exposed to the action of atmospheric oxygen for hours or days suffer no reoxidation and no post-darkening.

Keratin fibers or keratin-containing fibers should be understood to mean pelts, wool, feathers, and, in particular, human hair. Although the agents according to the invention are suitable predominantly for lightening and coloring keratin fibers or human hair, there is, in principle, nothing standing in the way of use in other fields.

The term "dyed keratin fibers" is understood to mean keratin fibers that have been dyed by means of traditional cosmetic dyeing agents known to a person skilled in the art. In particular, the term "dyed keratin fibers" should be understood to mean fibers that have been dyed by means of the oxidative dyeing agents known from the prior art and/or by means of direct dyes. In this context, the known monographs, e.g., Kh. Schrader, Grundlagen und Rezepturen der Kosmetika, $2^{nd}$ edition, Hüthig Buch Verlag, Heidelberg, 1989, that represent the corresponding knowledge of a person skilled in the art are expressly referenced.

The agents contain the ingredients essential to the invention preferably in a cosmetic carrier (agents (a) and (b)) or in an aqueous cosmetic carrier (agent (c)). The carriers can be, for example, a suitable aqueous or aqueous-alcoholic carrier. For the purpose of reductive decoloring, such carriers can be, for example, creams, emulsions, gels, or surfactant-containing foaming solutions, such as shampoos, foam aerosols, foam formulations, or other preparations suitable for use on hair. The agents for the reductive color removal of keratin fibers are especially preferably creams, emulsions, or flowable gels.

In particular, agent (a) can also be formulated water-free and can be present, for example, in solid form, as a powder or paste. Furthermore, agent (a) can also comprise a solvent-containing carrier or a carrier consisting of fat constituents such as fatty alcohols, fatty acid esters, hydrocarbons, silicone oils, and/or hydrophobic oils.

Agent (a) in Container (A)

The multi-component packaging unit (kit of parts) according to the invention comprises a first container (A), which is produced separately and which has a cosmetic agent (a). Agent (a) is characterized in that it includes, as a first ingredient (a1) essential to the invention, one or more reductants from the group comprising sodium dithionite, zinc dithionite, potassium dithionite, sodium sulfite, sodium hydrogen sulfite, potassium sulfite, potassium hydrogen sulfite, ammonium sulfite, sodium thiosulfate, potassium thiosulfate, ammonium thiosulfate, hydroxymethanesulfinic acid, aminomethanesulfinic acid, formamidine sulfinic acid, [bis(sulfinomethyl)amino]methanesulfinic acid, cysteine, thiolactic acid, thioglycolic acid, ascorbic acid, and/or the physiologically acceptable salts of the aforementioned acids.

Sodium dithionite is an inorganic reductant having the empirical formula $Na_2S_2O_4$ and the CAS no. 7775-14-6. Zinc dithionite is an inorganic reductant having the empirical formula $ZnS_2O_4$ and the CAS no. 7779-86-4. Potassium dithionite is an inorganic reductant having the empirical formula $K_2S_2O_4$ and the CAS no. 14293-73-3. Sodium sulfite is an inorganic reductant having the empirical formula $Na_2SO_3$ and the CAS no. 7757-83-7. Sodium hydrogen sulfite is an inorganic reductant having the empirical formula $NaHSO_3$ and the CAS no. 7631-90-5. Sodium hydrogen sulfite is preferably used in the form of an aqueous solution. Potassium sulfite is an inorganic reductant having the empirical formula $K_2SO_3$ and the CAS no. 10117-38-1. Potassium hydrogen sulfite is an inorganic reductant having the empirical formula $KHSO_3$ and the CAS no. 7773-03-7. Potassium hydrogen sulfite is preferably used in the form of an aqueous solution. Ammonium sulfite is an inorganic reductant having the empirical formula $(NH_4)_2SO_3$ and the CAS no. 10196-04-0.

Sodium thiosulfate is an inorganic reductant having the empirical formula $Na_2S_2O_3$ and the CAS no. 7772-98-7. Potassium thiosulfate is an inorganic reductant having the empirical formula $K_2S_2O_3$ and the CAS no. 10294-66-3. Ammonium thiosulfate is an inorganic reductant having the empirical formula $(NH_4)_2S_2O_3$ and the CAS no. 7783-18-8.

Hydroxymethanesulfinic acid is an organic reductant having the formula $HO-CH_2-S(O)OH$ and the CAS no. 79-25-4. Hydroxymethanesulfinic acid is alternatively also called formaldehydesulfoxylic acid. Both the use of hydroxymethanesulfinic acid itself and the use of the physiologically acceptable salts of hydroxymethanesulfinic acid, for example the sodium salt and/or the zinc salt, are in accordance with the invention. The use of sodium formaldehyde sulfoxylate (sodium hydroxymethanesulfinate, the sodium salt of hydroxymethanesulfinic acid) and/or zinc formaldehyde sulfoxylate (zinc hydroxymethanesulfinate, the zinc salt of hydroxymethanesulfinic acid) is therefore likewise in accordance with the invention.

Aminomethanesulfinic acid is an organic reductant having the formula $H_2N-CH_2-S(O)OH$ and the CAS no. 118201-33-5. Both the use of aminomethanesulfinic acid itself and the use of the physiologically acceptable salts of aminomethanesulfinic acid, for example the sodium salt and/or the zinc salt, are in accordance with the invention. The use of sodium aminomethane sulfinate (the sodium salt of aminomethanesulfinic acid) and/or zinc aminomethane sulfinate (the zinc salt of aminomethanesulfinic acid) is therefore likewise in accordance with the invention.

Formamidine sulfinic acid is alternatively also called thiourea dioxide or aminoiminomethanesulfinic acid. Formamidine sulfinic acid has the structure of formula (X1) but can also be present in the form of the tautomers thereof. Formamidine sulfinic acid has the CAS number 1758-73-2 and is commercially available from various suppliers, such as Sigma Aldrich.

(X1)

[Bis(sulfinomethyl)amino]methanesulfinic acid has the structure of formula (X2). Suitable physiologically acceptable salts of [bis(sulfinomethyl)amino]methanesulfinic acid are the sodium salt, the potassium salt, and the ammonium salt. In the case of all these salts, the three sulfinic acid groups are present in deprotonated form, wherein the electroneutrality is established by means of three sodium cations, three potassium cations, or three ammonium cations. The production of these compounds or the salts thereof is described, for example, in EP 0914516 B1.

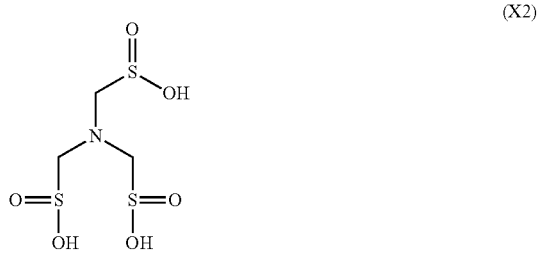 [SMILES: O=S(O)CN(CS(=O)O)CS(=O)O]

(X2)

According to the invention, cysteine (2-amino-3-sulfanylpropionic acid) is understood to mean D-cysteine, L-cysteine, and/or a mixture of D- and L-cysteine.

Thiolactic acid (2-sulfanylpropionic acid) is understood to mean D-thiolactic acid, L-thiolactic acid, and/or a mixture of D- and L-thiolactic acids. Both the use of thiolactic acid itself and the use of thiolactic acid in the form of a physiologically acceptable salt thereof are in accordance with the invention. A preferred salt of thiolactic acid is ammonium thiolactate.

Ammonium thiolactate is the ammonium salt of thiolactic acid (i.e., the ammonium salt of 2-sulfanylpropionic acid) (formula X3).

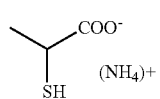

(formula X3)

The definition of ammonium thiolactate comprises both the ammonium salts of D-thiolactic acid and the ammonium salts of L-thiolactic acid, and mixtures thereof.

Sulfanylacetic acid (thioglycolic acid, 2-mercaptoacetic acid) is understood to mean an organic reductant of the formula HS—CH$_2$—COOH. The compound has the CAS no. 68-11-1. In the case of thioglycolic acid as well, both the use of thioglycolic acid itself and the use of a physiologically acceptable salt of thioglycolic acid are in accordance with the invention. For example, sodium thioglycolate, potassium thioglycolate, and/or ammonium thioglycolate can be used as physiologically acceptable salts of thioglycolic acid. Ammonium thioglycolate is a preferred physiologically acceptable salt of thioglycolic acid.

Ammonium thioglycolate is the ammonium salt of thioglycolic acid (i.e., the ammonium salt of sulfanylacetic acid) (formula X4).

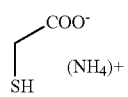

(formula X4)

According to the invention, ascorbic acid is understood to mean, in particular, (R)-5-[(S)-1,2-dihydroxyethyl]-3,4-dihydroxy-5H-furan-2-one (other alternative names: vitamin C, L-ascorbic acid) with the CAS no. 50-81-7.

The decoloring effect of the kit of parts according to the invention and the lastingness of this decoloration are determined, in part, both by the reductants (a1) included in agent (a) and by the post-treatment agent or the unsaturated acids (or acid derivatives) (c1) of formula (I) included therein.

The reductants from the group comprising sodium dithionite, zinc dithionite, potassium dithionite, formamidine sulfinic acid, [bis(sulfinomethyl)amino]methanesulfinic acid, and/or the physiologically acceptable salts of the aforementioned acids have been found to be especially well suited to reductively decoloring oxidatively dyed hair. The reductants from this group have proven especially highly compatible with the post-treatment agents (c) according to the invention.

An especially preferred multi-component packaging unit (kit of parts) is characterized in that agent (a) in container (A) contains (a1) one or more reductants from the group comprising sodium dithionite, zinc dithionite, potassium dithionite, formamidine sulfinic acid, [bis(sulfinomethyl)amino] methanesulfinic acid, and/or the physiologically acceptable salts of the aforementioned acids.

A physiologically acceptable salt is understood to be a salt of the aforementioned acids, wherein the acids have been converted into the ionic form thereof and have a physiologically acceptable counterion. A physiologically acceptable salt can be applied to the hair or to the skin without toxicological disadvantages arising, i.e., a physiologically acceptable salt of an aforementioned reductant is not more toxic and not more sensitizing than the reductant itself. Physiologically acceptable salts are, for example, the alkali-metal salts, the alkaline-earth-metal salts, or the ammonium salts of the aforementioned acids.

In other words, an especially preferred multi-component packaging unit (kit of parts) is characterized in that agent (a) in container (A) contains (a1) one or more reductants from the group comprising sodium dithionite, zinc dithionite, potassium dithionite, formamidine sulfinic acid, [bis(sulfinomethyl)amino] methanesulfinic acid, the sodium salt of [bis(sulfinomethyl)amino]methanesulfinic acid, the potassium salt of [bis(sulfinomethyl)amino]methanesulfinic acid, and/or the ammonium salt of [bis(sulfinomethyl)amino]methanesulfinic acid.

Furthermore, the one or more reductants from group (a) are preferably used in certain amount ranges. To obtain an optimal decoloring effect, it is preferred if the decoloring agent includes the one or more reductants (a1) in a total amount of 5.0 to 100 wt %, preferably 45.0 to 100 wt %, more preferably 65.0 to 100 wt %, and especially preferably 85.0 to 100 wt %, with respect to the total weight of agent (a).

An especially preferred multi-component packaging unit (kit of parts) is furthermore characterized in that agent (a) in container (A) contains—with respect to the total weight of agent (a)—

(a1) one or more reductants in a total amount of 5.0 to 100 wt %, preferably 45.0 to 100 wt %, more preferably 65.0 to 100 wt %, and especially preferably 85.0 to 100 wt %.

Also especially preferred is a multi-component packaging unit (kit of parts) for reductively decoloring dyed keratin fibers that is characterized in that agent (a) in container (A) contains (a1) one or more reductants from the group comprising sodium dithionite, zinc dithionite, potassium dithionite, and/or sodium thiosulfate in a total amount of 5.0 to 100 wt %, preferably 45.0 to 100 wt %, more preferably 65.0 to 100 wt %, and especially preferably 85.0 to 100 wt %, with respect to the total weight of agent (a).

Also especially preferred is a multi-component packaging unit (kit of parts) for reductively decoloring dyed keratin fibers that is characterized in that agent (a) in container (A) contains—with respect to the total weight of agent (a)—

(a1) formamidine sulfinic acid in an amount of 5.0 to 100 wt %, preferably 45.0 to 100 wt %, more preferably 65.0 to 100 wt %, and especially preferably 85.0 to 100 wt %.

Furthermore, it has been found to be especially advantageous if agents (a) according to the invention include certain combinations of reductants from group (a1), because an extremely strong decoloring effect occurs in the case of certain combinations. Especially advantageous in this context is the use of two different reductants from group (a1), wherein decoloring agent (a) includes (a11) a first reductant, which is selected from the group comprising sodium dithionite, zinc dithionite, potassium dithionite, sodium thiosulfate, potassium thiosulfate, and/ or ammonium thiosulfate, and additionally (a12) a second reductant, which is selected from the group comprising sodium sulfite, sodium hydrogen sulfite, potassium sulfite, potassium hydrogen sulfite, and/or ammonium sulfite.

Also special is a multi-component packaging unit for reductively decoloring dyed keratin fibers, more particularly human hair, wherein agent (a) in container (A) contains
(a11) formamidine sulfinic acid as a first reductant and
(a12) ascorbic acid as a second reductant.

Agent (b) in Container (B)

The multi-component packaging unit according to the invention comprises a second container (B), which is produced separately and which contains an agent (b). Said agent (b) is a cosmetic carrier formulation that can preferably be aqueous or aqueous-alcoholic. Extremely preferably, agent (b) is aqueous.

An extremely preferred multi-component packaging unit (kit of parts) is furthermore characterized in that agent (b) in container (B) contains (b1) water.

Shortly before the decoloring process, agents (a) and (b) are mixed to produce the ready-to-use decoloring agent.

Agent (b) is provided preferably as a liquid preparation, to which further surface-active substances can be added. They are selected preferably from anionic, zwitterionic, amphoteric, and nonionic surfactants and emulsifiers.

Agent (b) can include, for example, fatty acids, alkyl sulfates, alkyl ether sulfates, and ether carboxylic acids having 10 to 20 C atoms in the alkyl group and up to 16 glycol ether groups in the molecule as anionic surfactants.

Agent (b) can also include one or more zwitterionic surfactants, such as betaines, N-alkyl-N,N-dimethyl ammonium glycinates, N-acyl-aminopropyl-N,N-dimethyl ammonium glycinates, and 2-alkyl-3-carboxymethyl-3-hydroxyethyl imidazolines.

Agents (b) suitable according to the invention are furthermore characterized in that agent (b) additionally includes at least one amphoteric surfactant. Preferred amphoteric surfactants are N-alkyl glycines, N-alkyl propionic acids, N-alkyl aminobutyric acids, N-alkyl imino dipropionic acids, N-hydroxyethyl-N-alkyl amidopropyl glycines, N-alkyl taurines, N-alkyl sarcosines, 2-alkyl amino propionic acids, and alkyl amino acetic acids. Especially preferred amphoteric surfactants are N-coco alkylamino propionate, coco acylamino ethylamino propionate, and $C_{12}$-$C_{18}$ acyl sarcosine.

Furthermore, it has proven advantageous if agent (b) includes further, non-ionogenic interface-active substances. Preferred nonionic surfactants are alkyl polyglycosides and products of the addition of alkylene oxide to fatty alcohols, fatty acids and fatty acid glycerides having 2 to 50 moles of ethylene oxide per mole of fatty alcohol or fatty acid. Preparations having excellent properties are likewise obtained if they include fatty acid esters of ethoxylated glycerol as nonionic surfactants. It is extremely preferred if agent (b) includes, as a nonionic surfactant, an ethoxylated castor oil having 2 to 50 moles of ethylene oxide per mole of fatty acid or an ethoxylated, hydrogenated castor oil having 2 to 50 moles of ethylene oxide per mole of fatty acid. The use of PEG-40 Castor Oil is especially preferred in this context.

The non-ionic, zwitterionic, or amphoteric surfactants are used in fractions of 0.1 to 15.0 wt %, preferably 0.5 to 10.0 wt %, and extremely preferably 0.7 to 5.0 wt %, with respect to the total amount of the agent.

Various reductants pass through their effect optimum in a certain range of pH values. Ready-to-use decoloring agents having dithionite salts are preferably set to an acidic pH value, whereas ready-to-use decoloring agents having formamidine sulfinic acid develop their best effect in the alkaline range.

As already described above, the ready-to-use decoloring agent is produced shortly before use by mixing agents (a) and (b). For reasons of stability and storage, it is preferred to incorporate the alkalizing and acidifying agents into cosmetic carrier agent (b).

If a dithionite salt is selected as a reductant in agent (a), carrier agent (b) therefore preferably includes an acid. Accordingly, the pH value of aqueous carrier agent (b) also is preferably set to a value in the acidic range.

Within this embodiment, an especially preferred multi-component packaging unit (kit of parts) is characterized in that agent (a) in container (A) contains sodium dithionite, zinc dithionite, and/or potassium dithionite, and
agent (b) in container (B) contains
(b1) water and
(b2) one or more acids from the group of the inorganic and/or organic acids.

In particular, the acids citric acid, tartaric acid, malic acid, lactic acid, acetic acid, hydroxyethane-1,1-diphosphonic acid, methanesulfonic acid, benzoic acid, oxaloacetic acid, hydrochloric acid, sulfuric acid, phosphoric acid, malonic acid, and/or oxalic acid have been found to be suitable as acids in this context. The quick and complete dissolution of the thionite salts can be ensured by using one or more acids from this group in agent (b).

Within this embodiment, an especially preferred multi-component packaging unit (kit of parts) is characterized in that agent (b) in container (B) contains (b2) one or more acids from the group comprising citric acid, tartaric acid, malic acid, lactic acid, acetic acid, hydroxyethane-1,1-diphosphonic acid, methanesulfonic acid, benzoic acid, oxaloacetic acid, hydrochloric acid, sulfuric acid, phosphoric acid, malonic acid, and/or oxalic acid.

Therefore, the pH value of the aqueous agent preferably lies in the acidic range in this embodiment. Preferably, agent (b) is set to a pH value in the range of 1.0 to 6.0, preferably 1.2 to 5.0, more preferably 1.3 to 4.5, and especially preferably 1.4 to 4.0.

Within this embodiment, an extremely preferred multi-component packaging unit (kit of parts) is characterized in that agent (a) in container (A) contains sodium dithionite, zinc dithionite, and/or potassium dithionite, and
agent (b) in container (B) contains
(b1) water and
(b2) one or more acids from the group comprising citric acid, tartaric acid, malic acid, lactic acid, methanesulfonic acid, malonic acid, oxalic acid, and/or 1-hydroxyethane-1,1-diphosphonic acid.

If formamidine sulfinic acid is used as a reductant (a1) in agent (a), it was likewise possible to achieve excellent decoloring results. Formamidine sulfinic acid passes through its effect optimum at pH values in the alkaline range, i.e., the ready-to-use decoloring agent—and thus also agent (b)—preferably contain at least one alkalizing agent.

In this embodiment, an especially preferred multi-component packaging unit (kit of parts) is characterized in that agent (a) in container (A) contains formamidine sulfinic acid, and agent (b) in container (B) contains
- (b1) water and
- (b2') one or more alkalizing agents.

For example, basic amino acids such as arginine, lysine, ornithine, and/or histidine can be used as alkalizing agents in cosmetic carrier agent (b).

Other suitable alkalizing agents are inorganic alkalizing agents from the group comprising sodium hydroxide, potassium hydroxide, sodium carbonate, sodium hydrogencarbonate, potassium carbonate, potassium hydrogencarbonate, and/or ammonium carbonate.

In this context, nitrogen-containing alkalizing agents from the group comprising ammonia and/or alkanolamines have been found to be extremely suitable. Especially preferred alkanolamines can be selected, for example, from the group comprising ammonia, 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, and/or 2-amino-2-methylpropan-1,3-diol.

In this embodiment, an especially preferred multi-component packaging unit (kit of parts) is characterized in that agent (b) in container (B) contains
- (b2') one or more alkalizing agents from the group comprising ammonia, 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, and/or 2-amino-2-methylpropan-1,3-diol.

The pH value of the aqueous agent preferably lies in the alkaline range in this embodiment. Preferably, agent (b) is set to a pH value in the range of 7.0 to 12.0, preferably 7.5 to 11.0, more preferably 8.0 to 10.5, and especially preferably 8.0 to 10.0, within this embodiment.

Agent (c) in Container (C)

The multi-component packaging unit according to the invention also comprises a third container (C), which is produced separately and which contains agent (c). Agent (c) is an aqueous post-treatment agent that is applied to the keratin fibers after the application, after the action, and preferably after the rinsing out of the ready-to-use decoloring agent (i.e., the mixture of agents (a) and (b)).

The application of post-treatment agent (c) prevents the reoxidation or post-darkening, which otherwise usually always occurs when the reductively treated, decolored keratin fibers freed of the reductant by washing out are exposed to the action of atmospheric oxygen. To prevent post-darkening optimally, the post-treatment agent is applied preferably immediately after the decoloring agent (i.e., the mixture of agents (a) and (b)) has been rinsed out.

Essential to the invention for agent (c) is its content of at least one unsaturated acid of general formula (I),

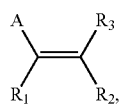
(I)

wherein
R1, R2, R3 represent, independently of each other, a hydrogen atom, a —CN group, a —COOM group, a —COOR4 group, a —CONR5R6 group, a phenyl residue, or a C1-C10 alkyl group,
M represents a hydrogen atom, an ammonium group $(NH_4)^+$, or an equivalent of a monovalent or multivalent alkali-metal or alkaline-earth-metal cation,
R4 represents a $C_1$-$C_6$ alkyl group,
R5, R6 represent, independently of each other, a hydrogen atom or a $C_1$-$C_6$ alkyl group,
A represents a —COOM group, a —COOR4 group, or a —(CH2)n-COOM group, and
n represents an integer from 1 to 10.

The substituents R1 to R5 of the compounds of formula (I) are illustrated by way of examples below:
Examples of a $C_1$-$C_6$ alkyl group are the groups methyl, ethyl, propyl, isopropyl, n-butyl, s-butyl, and t-butyl, n-pentyl, and n-hexyl. Propyl, ethyl, and methyl are preferred alkyl residues.

Furthermore, examples of the C1-C10 alkyl group are an n-octyl group, an isooctyl group, an n-nonyl group, and an n-decyl group.

Within the —COOM group, M can represent a hydrogen atom, an ammonium group $(NH_4)^+$, or an equivalent of a monovalent or multivalent alkali-metal or alkaline-earth-metal cation. If M represents a hydrogen atom, the —COOM group is present as a —COOH carboxylic acid group. If M represents an ammonium group $(NH_4)^+$, the compound is the ammonium salt of the acid.

An equivalent of a monovalent alkali-metal cation can be, for example, a sodium cation (—COONa) or potassium cation (—COOK).

An equivalent of a divalent alkaline-earth-metal cation can be, for example, $½Mg^{2+}$ or $½Ca^{2+}$. To preserve the electroneutrality, two carboxyl groups (—COO—) are neutralized by a $Mg^{2+}$ or a $Ca^{2+}$ cation in this case.

Residues R1, R2, and R3 represent, independently of each other, a hydrogen atom, a —CN group, a —COOM group, a —COOR4 group, a —CONR5R6 group, a phenyl residue, or a C1-C10 alkyl group.

Residues R1, R2, and R3 preferably represent, independently of each other, a hydrogen atom, a —COOM group, or a $C_1$-$C_{10}$ alkyl group.

In an extremely preferred embodiment, residue R1 represents a hydrogen atom, residue R2 represents a —COOM group, and residue R3 represents a hydrogen atom.

In another extremely preferred embodiment, residue R1 represents a hydrogen atom, residue R2 represents a hydrogen atom, and residue R3 represents a —COOM.

Residue A represents a —COOM group, a —COOR4 group, or a —(CH2)n-COOM group.

In an extremely preferred embodiment, residue A represents a —COOM group or a —(CH2)n-COOM group.

An especially preferred multi-component packaging unit (kit of parts) is furthermore characterized in that agent (c) in container (C) contains
(c1) one or more compounds of formula (I),

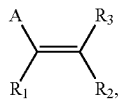
(I)

wherein

R1, R2, R3 represent, independently of each other, a hydrogen atom, a —COOM group, or a $C_1$-$C_{10}$ alkyl group, M represents a hydrogen atom, an ammonium group $(NH_4)^+$, or an equivalent of a monovalent or multivalent alkali-metal or alkaline-earth-metal cation, A represents a —COOM group or a —(CH2)n-COOM group, and n represents an integer from 1 to 10.

An extremely preferred multi-component packaging unit (kit of parts) is furthermore characterized in that agent (c) in container (C) contains (c1) one or more compounds of formula (I),

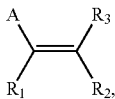

(I)

wherein

R1 represents a hydrogen atom,

R2, R3 represent, independently of each other, a hydrogen atom or a —COOM group, M represents a hydrogen atom, an ammonium group $(NH_4)^+$, or an equivalent of a monovalent or multivalent alkali-metal or alkaline-earth-metal cation, A represents a —COOM group or a —(CH2)n-COOM group, and n represents an integer from 1 to 10.

An extremely preferred multi-component packaging unit (kit of parts) is furthermore characterized in that agent (c) in container (C) contains (c1) one or more compounds of formula (I),

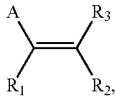

(I)

wherein

R1 represents a hydrogen atom,

R2 represents a hydrogen atom,

R3 represents a —COOM group,

M represents a hydrogen atom, an ammonium group $(NH_4)^+$, or an equivalent of a monovalent or multivalent alkali-metal or alkaline-earth-metal cation, and A represents a —COOM group.

The ability to suppress reoxidation depends essentially on the selection of unsaturated acid (c1), wherein specific acids have proven extremely effective.

Extremely suitable acids of formula (I) are selected from the group comprising maleic acid, fumaric acid, itaconic acid, oleic acid, palmitoleic acid, and/or physiologically acceptable salts thereof. It was possible to obtain the best results of all with maleic acid, fumaric acid, and/or the physiologically acceptable salts of these acids.

An extremely preferred multi-component packaging unit (kit of parts) is furthermore characterized in that agent (c) in container (C) contains (c1) one or more compounds of formula (I) from the group comprising maleic acid, fumaric acid, itaconic acid, oleic acid, palmitoleic acid, and/or physiologically acceptable salts thereof, extremely preferably maleic acid, fumaric acid, and/or physiologically acceptable salts thereof Maleic acid is alternatively also referred to as cis-butenedioic acid and has the CAS no. 11016-7. Suitable physiologically acceptable salts of maleic acid are the sodium salt, the potassium salt, and the ammonium salt.

Fumaric acid is the trivial name of trans-butenedioic acid. Fumaric acid has the CAS no. 11017-8. Suitable physiologically acceptable salts of fumaric acid are the sodium salt, the potassium salt, and the ammonium salt.

The unsaturated acid or the acids of formula (I) are used in this connection particularly to suppress the post-darkening. The use of certain amount ranges has proven especially good for solving the problem addressed by the invention.

Preferably, the acid or acids of formula (I) are used in a total amount of 0.1 to 20.0 wt %, preferably 0.5 to 15.0 wt %, more preferably 0.75 to 10.0 wt %, and extremely preferably 1.0 to 5.0 wt %. All amount specifications refer to the total amount of all acids of formula (I) included in agent (c), which total amount is expressed in relation to the total weight of agent (c).

An extremely preferred multi-component packaging unit (kit of parts) is furthermore characterized in that agent (c) in container (C) contains—with respect to the total weight of agent (c)—

(c1) one or more compounds of formula (I) in a total amount of 0.1 to 20.0 wt %, preferably 0.5 to 15.0 wt %, more preferably 0.75 to 10.0 wt %, and extremely preferably 1.0 to 5.0 wt %.

An explicitly extremely preferred multi-component packaging unit (kit of parts) is furthermore characterized in that agent (c) in container (C) contains—with respect to the total weight of agent (c)—

(c1) 0.1 to 20.0 wt %, preferably 0.5 to 15.0 wt %, more preferably 0.75 to 10.0 wt %, and extremely preferably 1.0 to 5.0 wt %, of maleic acid.

Another explicitly extremely preferred multi-component packaging unit (kit of parts) is furthermore characterized in that agent (c) in container (C) contains—with respect to the total weight of agent (c)—

(c1) 0.1 to 20.0 wt %, preferably 0.5 to 15.0 wt %, more preferably 0.75 to 10.0 wt %, and extremely preferably 1.0 to 5.0 wt %, of fumaric acid.

Post-treatment agent (c) can also include one or more further acids in addition to the unsaturated acids of formula (I). In particular, one or more acids from the group comprising citric acid, tartaric acid, malic acid, lactic acid, acetic acid, hydroxyethane-1,1-diphosphonic acid, methanesulfonic acid, benzoic acid, hydrochloric acid, sulfuric acid, phosphoric acid, malonic acid, oxaloacetic acid, and/or oxalic acid can be used as an additional acid.

An especially preferred multi-component packaging unit (kit of parts) is furthermore characterized in that agent (c) in container (C) additionally contains (c2) one or more acids from the group comprising citric acid, tartaric acid, malic acid, lactic acid, acetic acid, hydroxyethane-1,1-diphosphonic acid, methanesulfonic acid, benzoic acid, hydrochloric acid, sulfuric acid, phosphoric acid, malonic acid, oxaloacetic acid, and/or oxalic acid.

In particular, citric acid, tartaric acid, malic acid, and/or lactic acid has proven especially suitable for joint use with maleic acid and/or fumaric acid. For example, by using a mixture of maleic acid and citric acid, it was possible to improve the decoloring effect further in comparison with the use of one of the acids alone.

A preferred multi-component packaging unit (kit of parts) is furthermore characterized in that agent (c) in container (C) contains—with respect to the total weight of agent (c)—

(c2) one or more acids from the group comprising citric acid, tartaric acid, malic acid, lactic acid, acetic acid, hydroxyethane-1,1-diphosphonic acid, methanesulfonic acid, benzoic acid, hydrochloric acid, sulfuric acid, phosphoric acid, malonic acid, and/or oxalic acid in a total amount of 0.1 to 20.0 wt %, preferably 0.5 to 15.0 wt %, more preferably 0.75 to 10.0 wt %, and especially preferably 1.0 to 5.0 wt %.

An explicitly extremely preferred multi-component packaging unit (kit of parts) is furthermore characterized in that agent (c) in container (C) contains—with respect to the total weight of agent (c)—
(c1) 0.1 to 20.0 wt % of maleic acid and
(c2) 0.1 to 20.0 wt % of citric acid.

An explicitly extremely preferred multi-component packaging unit (kit of parts) is furthermore characterized in that agent (c) in container (C) contains—with respect to the total weight of agent (c)—
(c1) 0.5 to 15.0 wt % of maleic acid and
(c2) 0.5 to 15.0 wt % of citric acid.

An explicitly extremely preferred multi-component packaging unit (kit of parts) is furthermore characterized in that agent (c) in container (C) contains—with respect to the total weight of agent (c)—
(c1) 0.75 to 10.0 wt % of maleic acid and
(c2) 0.75 to 10.0 wt % of citric acid.

An explicitly extremely preferred multi-component packaging unit (kit of parts) is furthermore characterized in that agent (c) in container (C) contains—with respect to the total weight of agent (c)—
(c1) 1.0 to 5.0 wt % of maleic acid and
(c2) 1.0 to 5.0 wt % of citric acid.

An explicitly extremely preferred multi-component packaging unit (kit of parts) is furthermore characterized in that agent (c) in container (C) contains—with respect to the total weight of agent (c)—
(c1) 0.1 to 20.0 wt % of fumaric acid and
(c2) 0.1 to 20.0 wt % of citric acid.

An explicitly extremely preferred multi-component packaging unit (kit of parts) is furthermore characterized in that agent (c) in container (C) contains—with respect to the total weight of agent (c)—
(c1) 0.5 to 15.0 wt % of fumaric acid and
(c2) 0.5 to 15.0 wt % of citric acid.

An explicitly extremely preferred multi-component packaging unit (kit of parts) is furthermore characterized in that agent (c) in container (C) contains—with respect to the total weight of agent (c)—
(c1) 0.75 to 10.0 wt % of fumaric acid and
(c2) 0.75 to 10.0 wt % of citric acid.

An explicitly extremely preferred multi-component packaging unit (kit of parts) is furthermore characterized in that agent (c) in container (C) contains—with respect to the total weight of agent (c)—
(c1) 1.0 to 5.0 wt % of fumaric acid and
(c2) 1.0 to 5.0 wt % of citric acid.

An explicitly extremely preferred multi-component packaging unit (kit of parts) is furthermore characterized in that agent (c) in container (C) contains—with respect to the total weight of agent (c)—
(c1) 0.1 to 20.0 wt % of maleic acid and
(c2) 0.1 to 20.0 wt % of tartaric acid.

An explicitly extremely preferred multi-component packaging unit (kit of parts) is furthermore characterized in that agent (c) in container (C) contains—with respect to the total weight of agent (c)—
(c1) 0.5 to 15.0 wt % of maleic acid and
(c2) 0.5 to 15.0 wt % of tartaric acid.

An explicitly extremely preferred multi-component packaging unit (kit of parts) is furthermore characterized in that agent (c) in container (C) contains—with respect to the total weight of agent (c)—
(c1) 0.75 to 10.0 wt % of maleic acid and
(c2) 0.75 to 10.0 wt % of tartaric acid.

An explicitly extremely preferred multi-component packaging unit (kit of parts) is furthermore characterized in that agent (c) in container (C) contains—with respect to the total weight of agent (c)—
(c1) 1.0 to 5.0 wt % of maleic acid and
(c2) 1.0 to 5.0 wt % of tartaric acid.

An explicitly extremely preferred multi-component packaging unit (kit of parts) is furthermore characterized in that agent (c) in container (C) contains—with respect to the total weight of agent (c)—
(c1) 0.1 to 20.0 wt % of fumaric acid and
(c2) 0.1 to 20.0 wt % of tartaric acid.

An explicitly extremely preferred multi-component packaging unit (kit of parts) is furthermore characterized in that agent (c) in container (C) contains—with respect to the total weight of agent (c)—
(c1) 0.5 to 15.0 wt % of fumaric acid and
(c2) 0.5 to 15.0 wt % of tartaric acid.

An explicitly extremely preferred multi-component packaging unit (kit of parts) is furthermore characterized in that agent (c) in container (C) contains—with respect to the total weight of agent (c)—
(c1) 0.75 to 10.0 wt % of fumaric acid and
(c2) 0.75 to 10.0 wt % of tartaric acid.

An explicitly extremely preferred multi-component packaging unit (kit of parts) is furthermore characterized in that agent (c) in container (C) contains—with respect to the total weight of agent (c)—
(c1) 1.0 to 5.0 wt % of fumaric acid and
(c2) 1.0 to 5.0 wt % of tartaric acid.

An explicitly extremely preferred multi-component packaging unit (kit of parts) is furthermore characterized in that agent (c) in container (C) contains—with respect to the total weight of agent (c)—
(c1) 0.1 to 20.0 wt % of maleic acid and
(c2) 0.1 to 20.0 wt % of malic acid.

An explicitly extremely preferred multi-component packaging unit (kit of parts) is furthermore characterized in that agent (c) in container (C) contains—with respect to the total weight of agent (c)—
(c1) 0.5 to 15.0 wt % of maleic acid and
(c2) 0.5 to 15.0 wt % of malic acid.

An explicitly extremely preferred multi-component packaging unit (kit of parts) is furthermore characterized in that agent (c) in container (C) contains—with respect to the total weight of agent (c)—
(c1) 0.75 to 10.0 wt % of maleic acid and
(c2) 0.75 to 10.0 wt % of malic acid.

An explicitly extremely preferred multi-component packaging unit (kit of parts) is furthermore characterized in that agent (c) in container (C) contains—with respect to the total weight of agent (c)—
(c1) 1.0 to 5.0 wt % of maleic acid and
(c2) 1.0 to 5.0 wt % of malic acid.

An explicitly extremely preferred multi-component packaging unit (kit of parts) is furthermore characterized in that agent (c) in container (C) contains—with respect to the total weight of agent (c)—
(c1) 0.1 to 20.0 wt % of fumaric acid and
(c2) 0.1 to 20.0 wt % of malic acid.

An explicitly extremely preferred multi-component packaging unit (kit of parts) is furthermore characterized in that agent (c) in container (C) contains—with respect to the total weight of agent (c)—
(c1) 0.5 to 15.0 wt % of fumaric acid and
(c2) 0.5 to 15.0 wt % of malic acid.

An explicitly extremely preferred multi-component packaging unit (kit of parts) is furthermore characterized in that agent (c) in container (C) contains—with respect to the total weight of agent (c)—
(c1) 0.75 to 10.0 wt % of fumaric acid and
(c2) 0.75 to 10.0 wt % of malic acid.

An explicitly extremely preferred multi-component packaging unit (kit of parts) is furthermore characterized in that agent (c) in container (C) contains—with respect to the total weight of agent (c)—
(c1) 1.0 to 5.0 wt % of fumaric acid and
(c2) 1.0 to 5.0 wt % of malic acid.

An explicitly extremely preferred multi-component packaging unit (kit of parts) is furthermore characterized in that agent (c) in container (C) contains—with respect to the total weight of agent (c)—
(c1) 0.1 to 20.0 wt % of maleic acid and
(c2) 0.1 to 20.0 wt % of lactic acid.

An explicitly extremely preferred multi-component packaging unit (kit of parts) is furthermore characterized in that agent (c) in container (C) contains—with respect to the total weight of agent (c)—
(c1) 0.5 to 15.0 wt % of maleic acid and
(c2) 0.5 to 15.0 wt % of lactic acid.

An explicitly extremely preferred multi-component packaging unit (kit of parts) is furthermore characterized in that agent (c) in container (C) contains—with respect to the total weight of agent (c)—
(c1) 0.75 to 10.0 wt % of maleic acid and
(c2) 0.75 to 10.0 wt % of lactic acid.

An explicitly extremely preferred multi-component packaging unit (kit of parts) is furthermore characterized in that agent (c) in container (C) contains—with respect to the total weight of agent (c)—
(c1) 1.0 to 5.0 wt % of maleic acid and
(c2) 1.0 to 5.0 wt % of lactic acid.

An explicitly extremely preferred multi-component packaging unit (kit of parts) is furthermore characterized in that agent (c) in container (C) contains—with respect to the total weight of agent (c)—
(c1) 0.1 to 20.0 wt % of fumaric acid and
(c2) 0.1 to 20.0 wt % of lactic acid.

An explicitly extremely preferred multi-component packaging unit (kit of parts) is furthermore characterized in that agent (c) in container (C) contains—with respect to the total weight of agent (c)—
(c1) 0.5 to 15.0 wt % of fumaric acid and
(c2) 0.5 to 15.0 wt % of lactic acid.

An explicitly extremely preferred multi-component packaging unit (kit of parts) is furthermore characterized in that agent (c) in container (C) contains—with respect to the total weight of agent (c)—
(c1) 0.75 to 10.0 wt % of fumaric acid and
(c2) 0.75 to 10.0 wt % of lactic acid.

An explicitly extremely preferred multi-component packaging unit (kit of parts) is furthermore characterized in that agent (c) in container (C) contains—with respect to the total weight of agent (c)—
(c1) 1.0 to 5.0 wt % of fumaric acid and
(c2) 1.0 to 5.0 wt % of lactic acid.

To achieve the best possible decoloring result, unsaturated acids (c1) of formula (I) and the additional acids of group (c2) are preferably used in a certain amount ratio to each other. It was possible to observe the best inhibition of reoxidation when agent (c) in container (C) contained one or more compounds (c1) of formula (I) and one or more acids of group (c2) in a weight ratio (c1)/(c2) of 10:1 to 1:10, preferably 3:1 to 1:3, and especially preferably 3:2 to 2:3.

An additionally extremely preferred multi-component packaging unit (kit of parts) is thus characterized in that agent (c) in container (C) contains
one or more compounds (c1) of formula (I) and one or more acids of group (c2) in a weight ratio (c1)/(c2) of 10:1 to 1:10, preferably 3:1 to 1:3, and especially preferably 3:2 to 2:3.

Example: 100 g of aqueous agent (C) contain
(c1) 2.5 g (corresponds to 2.5 wt %) of maleic acid and
(c2) 2.5 g (corresponds to 2.5 wt %) of citric acid.
The weight ratio of (c1)/(c2) is (2.5/2.5)=1:1.

An additionally extremely preferred multi-component packaging unit (kit of parts) is thus characterized in that
agent (a) in container (A) is a water-free agent,
agent (b) in container (B) is an aqueous agent, and
agent (c) in container (C) has a pH value of 0.5 to 4.0, preferably 0.7 to 3.5, more preferably 0.9 to 3.0, and especially preferably 0.9 to 2.5.

All pH values of the present invention were measured with a glass electrode of type N 61 from Schott at a temperature of 22° C.

Agents (a), (b), and/or (c) according to the invention can additionally include at least one oil component. Oil components suitable according to the invention are, in principle, all oils and fatty substances and mixtures thereof with solid paraffins and waxes. Such oil components whose solubility in water at 20° C. is less than 1 wt %, more particularly less than 0.1 wt %, are preferred. The melting point of the individual oil or fat components is preferably below approximately 40° C. Oil components that are liquid at room temperature, i.e., below 25° C., can be especially preferred according to the invention. However, if several oil and fat components and possibly solid paraffins and waxes are used, it is generally also sufficient if the mixture of the oil and fat components and possibly paraffins and waxes satisfies these conditions.

A preferred group of oil components are plant oils. Examples of such oils are apricot kernel oil, avocado oil, sunflower oil, olive oil, soy oil, rape oil, almond oil, jojoba oil, orange oil, wheat germ oil, peach kernel oil, and the liquid fractions of coconut oil. Other triglyceride oils, such as the liquid fractions of beef tallow and synthetic triglyceride oils, are also suitable.

A further, especially preferred group of oil components that can be used according to the invention are liquid paraffin oils and synthetic hydrocarbons and di-n-alkyl ethers having a total of 12 to 36 C atoms, more particularly 12 to 24 C atoms, such as di-n-octyl ether, di-n-decyl ether, di-n-nonyl ether, di-n-undecyl ether, di-n-dodecyl ether, n-hexyl n-octyl ether, n-octyl n-decyl ether, n-decyl n-undecyl ether, n-undecyl n-dodecyl ether, and n-hexyl n-undecyl ether, and di-tert-butyl ether, diisopentyl ether, di-3-ethyldecyl ether, tert-butyl n-octyl ether, isopentyl n-octyl ether, and 2-methylpentyl n-octyl ether. The compounds 1,3-di(2-ethylhexyl)-cyclohexane (Cetiol® S) and di-n-octyl ether (Cetiol® OE), which are available as commercial products, can be preferred.

Fatty acid esters and fatty alcohol esters are oil components that likewise can be used according to the invention. The monoesters of the fatty acids with alcohols having 3 to 24 C atoms are preferred. This group of substances comprises the products of the esterification of fatty acids having 8 to 24 C atoms, such as caproic acid, caprylic acid, 2-ethylhexanoic acid, capric acid, lauric acid, isotridecanoic acid, myristic acid, palmitic acid, palmoleic acid, stearic acid, isostearic acid, oleic acid, elaidic acid, petroselinic acid, linoleic acid, linolenic acid, elaeostearic acid, arachidic acid, gadoleic acid, behenic acid, and erucic acid and technical mixtures thereof, which arise, for example, when natural fats and oils are subjected to high-pressure splitting, when aldehydes from Roelen oxo synthesis are reduced, or when unsaturated fatty acids are dimerized, with alcohols such as isopropyl alcohol, glycerol, caproic alcohol, capryl alcohol, 2-ethylhexanol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol, and brassidyl alcohol and technical mixtures thereof, which arise, for example, when technical methyl esters based on fats and oils or aldehydes from Roelen oxo synthesis are subjected to high-pressure hydrogenation and which arise as a monomer fraction when unsaturated fatty alcohols are dimerized. Isopropyl myristate, isononaoic acid C16-18 alkyl ester (Cetiol® SN), stearic acid 2-ethylhexyl ester (Cetiol® 868), cetyl oleate, glycerol tricaprylate, coconut fatty alcohol caprate/caprylate, and n-butyl stearate are especially preferred according to the invention.

Dicarboxylic acid esters such as di-n-butyl adipate, di(2-ethylhexyl) adipate, di(2-ethylhexyl) succinate, and diisotridecyl acelaate, and diol esters such as ethylene glycol dioleate, ethylene glycol diisotridecanoate, propylene glycol di(2-ethylhexanoate), propylene glycol diisostearate, propylene glycol dipelargonate, butanediol diisostearate, and neopentyl glycol dicaprylate, as well as complex esters such as diacetyl glycerol monostearate, are also oil components that can be used according to the invention.

Finally, silicone oils, in particular dialkyl and alkylaryl siloxanes, such as dimethylpolysiloxane and methyl phenyl polysiloxane, and their alkoxylated and quaternized analogs, and cyclic siloxanes are also oil components that can be preferably used according to the invention. Examples of such silicones are the products sold by Dow Corning under the names DC 190, DC 200, and DC 1401 and the commercial products DC 344 and DC 345 from Dow Corning, Q2-7224 (manufacturer: Dow Corning; a stabilized trimethylsilylamodimethicone), Dow Corning® 929 Emulsion (including a hydroxylamino-modified silicone, which is also referred to as amodimethicone), SM-2059 (manufacturer: General Electric), SLM-55067 (manufacturer: Wacker), and Abir-Quat 3270 and 3272 (manufacturer: Th. Goldschmidt; diquaternary polydimethylsiloxanes, Quaternium-80), are also oil components that can be preferably used according to the invention. Silicone oils having a kinematic viscosity of up to 50,000 cSt measured at 25° C. can be preferred according to the invention. Extremely preferred are silicone oils having kinematic viscosities of up to 10,000 cSt measured at 25° C. The viscosities are determined in accordance with the ball-drop method per the method of British Standard 188. Comparable values are obtained with testing instructions of the manufacturers analogous to British Standard 188, for example CTM 0577 of Dow Corning Corporation.

In a special embodiment, cyclic siloxanes in particular, such as the products Dow Corning® 344, Dow Corning® 345, Dow Corning® 244, Dow Corning® 245, or Dow Corning® 246, having kinematic viscosities of up to 10,000 cSt at 25° C. determined according to the manufacturer's specifications are used as an oil component.

Finally, dialkyl carbonates, which are described in detail in laid-open application DE 197 101 54, which is expressly referenced, are also oil components that can be used according to the invention. Dioctyl carbonates, in particular di-2-ethylhexyl carbonate, are preferred oil components in the present invention.

Furthermore, agents (a), (b), and/or (c) according to the invention can additionally include alcohols that are miscible with water only to a limited extent.

"Miscible with water to a limited extent" is understood to mean alcohols that have a solubility in water at 20° C. of no more than 10 wt %, with respect to the water mass.

In many cases, triols and in particular diols have proven especially suitable according to the invention. Alcohols having 4 to 20, more particularly 4 to 10, carbon atoms can be used according to the invention. The alcohols used according to the invention can be saturated or unsaturated and linear, branched, or cyclic. For example, butanol-1, cyclohexanol, pentanol-1, decanol, octanol, octenol, dodecenol, decenol, octadienol, dodecadienol, decadienol, oleyl alcohol, eruca alcohol, ricinol alcohol, stearyl alcohol, isostearyl alcohol, cetyl alcohol, lauryl alcohol, myristyl alcohol, arachidyl alcohol, capryl alcohol, capric alcohol, linoleyl alcohol, linolenyl alcohol, and behenyl alcohol and the Guerbet alcohols thereof can be used according to the invention, wherein this list should be understood to provide examples and to be unrestrictive. However, the fatty alcohols are derived from preferably natural fatty acids, wherein it can usually be assumed that the fatty alcohols are obtained from the esters of the fatty acids by reduction. Fatty alcohol cuts that are produced by reducing naturally occurring triglycerides such as beef tallow, palm oil, peanut oil, colza oil, cottonseed oil, soy oil, sunflower oil, and linseed oil or fatty acid esters arising from the products of the transesterification of said triglycerides with corresponding alcohols, and thus are a mixture of different fatty alcohols, are also usable according to the invention.

2-Ethylhexanediol-1,3, butanol-1, cyclohexanol, pentanol-1, and 1,2-butanediol are preferred as alcohols according to the invention. In particular, 2-ethylhexanediol-1,3, butanol-1, and cyclohexanol are especially preferred.

In a further embodiment, emulsifiers can be used in agents (a), (b), and/or (c) according to the invention. Emulsifiers cause the formation of water- or oil-stable adsorption layers at the phase interface, which adsorption layers protect the dispersed drops against coalescence and thus stabilize the emulsion. Therefore, like surfactants, emulsifiers are constructed of a hydrophobic molecule part and a hydrophilic molecule part. Hydrophilic emulsifiers preferably form O/W emulsions and hydrophobic emulsifiers preferably form W/O emulsions. The term "emulsion" should be understood to mean a distribution (dispersion), in the form of drops, of a liquid in another liquid achieved by applying energy in order to create stabilizing phase interfaces by means of surfactants. The selection of these emulsifying surfactants or emulsifiers is based on the substances to be dispersed and the outer phase and the fineness of the emulsion. More detailed definitions and properties of emulsifiers are found in "H.-D. Dörfler, Grenzflächen- and Kolloidchemie, VCH Verlagsgesellschaft mbH. Weinheim, 199." Emulsifiers that can be used according to the invention are, for example,
- products of the addition of 4 to 100 mol of ethylene oxide and/or 0 to 5 mol of propylene oxide to linear fatty alcohols having 8 to 22 C atoms, to fatty acids having 12 to 22 C atoms, and to alkylphenols having 8 to 15 C atoms in the alkyl group,
- $C_{12}$-$C_{22}$ fatty acid mono- and diesters of products of the addition of 1 to 30 mol of ethylene oxide to polyols having 3 to 6 carbon atoms, more particularly to glycerol,
- products of the addition of ethylene oxide and polyglycerol to methylglucoside fatty acid esters, fatty acid alkanolamides, and fatty acid glucamides,
- $C_8$-$C_{22}$ alkyl mono- and oligoglycosides and ethoxylated analogs thereof, wherein degrees of oligomerization of 1.1 to 5, more particularly 1.2 to 2.0, and glucose as a sugar component are preferred,
- mixtures of alkyl (oligo)glucosides and fatty alcohols, for example the commercially available product Montanov® 68,
- products of the addition of 5 to 60 mol of ethylene oxide to castor oil and hardened castor oil,
- partial esters of polyols having 3-6 carbon atoms with saturated fatty acids having 8 to 22 C atoms,
- sterols. The term "sterols" is understood to mean a group of steroids that bear a hydroxyl group at C atom 3 of the steroid skeleton and are isolated both from animal tissue (zoosterols) and from plant fats (phytosterols). Examples of zoosterols are cholesterol and lanosterol. Examples of suitable phytosterols are ergosterol, stigmasterol, and sitosterol. Sterols (the mycosterols) are also isolated from fungi and yeasts.
- phospholipids. The term "phospholipids" is understood to mean, above all, the glucose phospholipids, which are obtained, for example, as lecithins or phosphatidylcholines from, for example, egg yolk or plant seeds (e.g., soybeans).
- fatty acid esters of sugars and sugar alcohols, such as sorbitol,
- polyglycerols and polyglycerol derivatives such as polyglycerol poly-12-hydroxystearate (commercial product Dehymuls® PGPH),
- linear and branched fatty acids having 8 to 30 C atoms and the Na, K, Ca, Mg, and Zn salts thereof.

The agents according to the invention include the emulsifiers preferably in amounts of 0.1 to 25 wt %, more particularly 0.1 to 3 wt %, with respect to the particular total composition.

The agents according to the invention can preferably include at least one non-ionogenic emulsifier having an HLB of 8 to 18 in accordance with the definitions provided in Römpp-Lexikon Chemie (editors J. Falbe, M. Regitz), 10$^{th}$ edition, Georg Thieme Verlag Stuttgart, New York, (1997), page 1764. Non-ionogenic emulsifiers having an HLB of 10 to 15 can be especially preferred according to the invention.

Furthermore, it has proven advantageous if the agents according to the invention include a care-providing active substance, selected from protein hydrolysates and derivatives thereof Suitable protein hydrolysates are, in particular, hydrolysates of elastin, collagen, keratin, milk, egg white, silk protein, almond protein, pea protein, potato protein, oat protein, corn protein, and wheat protein. Plant-based products can be preferred according to the invention.

Suitable derivatives are, in particular, quaternized protein hydrolysates. Examples of this compound class are the products found on the market under the names Lamequat® L (CTFA designation: Lauryldimonium Hydroxypropylamino Hydrolyzed Animal Protein; Grünau), Croquat® WKP, and Gluadin® WQ. The last-mentioned product, which is plant-based, can be preferred.

The protein derivatives are included in the agents according to the invention preferably in amounts of 0.1 to 10 wt %, with respect to the total amount of the agent. Amounts of 0.1 to 5 wt % are preferred.

Agents (a), (b), and/or (c) preferably also include at least one conditioning active substance.

Cationic polymers are preferably considered as conditioning active substances. They are generally polymers that include a quaternary nitrogen atom, for example in the form of an ammonium group.

Preferred cationic polymers are, for example,
- quaternized cellulose derivatives, which are commercially available under the names Celquat® and Polymer JR®; the compounds Celquat® H 100, Celquat® L 200, and Polymer JR® 400 are preferred quaternized cellulose derivatives,
- polysiloxanes having quaternary groups,
- polymeric dimethyldiallylammonium salts and copolymers thereof with esters and amides of acrylic acid and methacrylic acid. The products commercially available under the names Merquat® 100 (poly(dimethyldiallylammonium chloride)) and Merquat® 550 (dimethyldiallylammoniumchloride/acrylamide copolymer) are examples of such cationic polymers.
- copolymers of vinylpyrrolidone with quaternized derivatives of dialkylamino acrylate and methacrylate, such as vinylpyrrolidone/dimethylamino methacrylate copolymers quaternized with diethyl sulfate. Such compounds are commercially available under the names Gafquat® 734 and Gafquat® 755.
- vinylpyrrolidone/vinylimidazolinium methochloride copolymers, which are offered under the name Luviquat®,
- quaternized polyvinyl alcohol,
- and the polymers known under the names
  - Polyquaternium 2,
  - Polyquaternium 17,
  - Polyquaternium 18, and
  - Polyquaternium 27 having quaternary nitrogen atoms in the polymer main chain.

Amphopolymers are also suitable as conditioning active substances. The general term "amphopolymers" comprises amphoteric polymers, i.e., polymers that include both free amino groups and free —COOH— or $SO_3H$ groups in the molecule and are capable of forming inner salts, zwitterionic polymers, which include quaternary ammonium groups and —COO$^-$ or —$SO_3^-$ groups in the molecule, and polymers that include —COOH— or $SO_3H$ groups and quaternary ammonium groups. An example of an amphopolymer that can be used according to the invention is the acrylic resin available under the name Amphomer®, which is a copolymer of tert-butylaminoethyl methacrylate, N-(1,1,3,3-tetramethylbutyl)acrylamide, and two or more monomers from the group comprising acrylic acid, methacrylic acid, and the simple esters thereof. Likewise preferred amphopolymers are composed of unsaturated carboxylic acids (e.g., acrylic and methacrylic acid), cationically derivatized unsaturated carboxylic acids (e.g., acrylamidopropyl trimethylammonium chloride), and possibly further ionic or non-ionogenic monomers, as can be found, for example, in the German laid-open application 39 29 973 and the prior art cited there. Terpolymers of acrylic acid, methyl acrylate, and methacrylamidopropyl trimonium chloride, which are commercially available under the name Merquat® 2001 N, and the commercial product Merquat® 280 are amphopolymers that are especially preferred according to the invention.

The cationic or amphoteric polymers are included in the preparations according to the invention preferably in amounts of 0.1 to 5 wt %, with respect to the total preparation.

Silicone gums, such as the commercial product Fancorsil® LIM-1, and anionic silicones, such as the product Dow Corning® 1784, are also suitable as conditioning active substances.

Examples of the cationic surfactants that can be used as conditioning active substances in the agents according to the invention are, in particular, quaternary ammonium compounds. Ammonium halides, more particularly chlorides and bromides, such as alkyltrimethylammonium chlorides, dialkyldimethylammonium chlorides, and tiralkylmethylammonium chlorides, for example cetyltrimethylammonium chloride, stearyltrimethylammonium chloride, distearyldimethylammonium chloride, lauryldimethylammonium chloride, lauryldimethylbenzylammonium chloride, and tricetylmethylammonium chloride, are preferred. Furthermore, the highly biodegradable quaternary ester compounds, so-called "esterquats," such as the methyl hydroxyalkyl dialkoyloxyalkyl ammonium methosulfates sold under the trademarks Dehyquart® and Stepantex®, can be used.

Alkyl amido amines, in particular fatty acid amido amines such as the stearamidopropyl dimethylamine available under the name Tego Amid® S 18, are distinguished especially by their good biodegradability in addition to good conditioning action.

Furthermore, it can be preferred to tint the individual phases with dyes to achieve an especially good optical appearance of the agent. These dyes are soluble preferably only in the aqueous phase or only in at least one non-aqueous phase in an amount that makes a corresponding coloring visible to the observer. It is also possible to dye both the non-aqueous phase and the aqueous phase with different dyes, preferably in different colors. However, the tinting of only a non-aqueous phase is preferred.

Further common constituents for the agents according to the invention are:
- anionic surfactants, such as soaps, alkyl sulfates, and alkyl polyglycol ether sulfates, salts of ether carboxylic acids of the formula R—O—($CH_2$—$CH_2O$)$_x$—$CH_2$—COOH, in which R is a linear alkyl group having 10 to 22 C atoms and x is 0 or 1 to 16, acyl sarcosides, acyl taurides, acyl isethionates, sulfosuccinic acid mono- and dialkyl esters, linear alkane sulfonates, linear alpha-olefin sulfonates, alpha-sulfo fatty acid methyl esters, and esters of tartaric acid and citric acid alkyl glycosides or alcohols that are products of the addition of approximately 2-15 molecules of ethylene oxide and/or propylene oxide to fatty alcohols having 8 to 22 C atoms,
- zwitterionic surfactants such as betaines and 2-alkyl-3-carboxymethyl-3-hydroxyethyl imidazolines,
- ampholytic surfactants, such as N-alkyl glycines, N-alkyl propionic acids, N-alkyl aminobutyric acids, N-alkyl imino dipropionic acids, N-hydroxyethyl-N-alkyl amidopropyl glycines, N-alkyl taurines, N-alkyl sarcosines, 2-alkyl amino propionic acids, and alkyl amino acetic acids,
- nonionic surfactants, such as products of the addition of 2 to 30 mol of ethylene oxide and/or 0 to 5 mol of propylene oxide to linear fatty alcohols having 15 to 22 C atoms, to fatty acids having 12 to 22 C atoms, and to alkylphenols having 8 to 15 C atoms in the alkyl group, $C_{12}$-$C_{22}$ fatty acid mono- and diesters of products of the addition of 1 to 30 mol of ethylene oxide to glycerol, $C_8$-$C_{22}$ alkyl mono- and oligoglycosides and ethoxylated analogs thereof, and products of the addition of 5 to 60 mol of ethylene oxide to castor oil and hardened castor oil,
- non-ionic polymers such as vinylpyrrolidone/vinyl acrylate copolymers, polyvinylpyrrolidone, and vinylpyrrolidone/vinyl acetate copolymers,
- anionic polymers, such as polyacrylic and polymethacrylic acids, salts thereof, copolymers thereof with acrylic acid and methacrylic acid esters and amides, and derivatives thereof obtained by crosslinking with polyfunctional agents, polycarboxylic acids, such as polyketocarboxylic and polyaldehydocarboxylic acids and salts thereof, and polymers and copolymers of crotonic acid with esters and amides of acrylic acid and methacrylic acid, such as vinyl acetate/crotonic acid and vinyl acetate/vinyl propionate/crotonic acid copolymers,
- organic thickeners, such as agar-agar, guar gum, alginates, cellulose ethers, such as methyl and methyl hydroxypropyl cellulose, gelatin, pectins, and/or xanthan gum. Ethoxylated fatty alcohols, in particular those having limited homolog distribution, which are on the market as a commercial product under the name Arlypon® F (Henkel) for example, alkoxylated methylglucoside esters, such as the commercial product Glucamate® DOE 120 (Amerchol), and ethoxylated propylene glycol esters, such as the commercial product Antil® 141 (Goldschmidt), can be preferred organic thickeners.
- structurants such as glucose and maleic acid,
- hair-conditioning compounds such as phospholipids, for example soy lecithin, egg lecithin, and cephalins,
- perfume oils,
- solubilizers, such as ethanol, isopropanol, ethylene glycol, propylene glycol, glycerol, diethylene glycol, and ethoxylated triglycerides, and fatty alcohol ethoxylates and derivatives thereof,
- anti-dandruff active substances such as climbazole, piroctone olamine, and Zinc Omadine,
- active substances such as bisabolol, allantoin, panthenol, niacinamide, tocopherol, and plant extracts,
- light stabilizers,
- consistency regulators such as sugar esters, polyolesters, or polyol alkyl ethers,
- fatty acid alkanolamides,
- complexing agents such as EDTA, NTA, β-alanine diacetic acid, and phosphonic acids,
- swelling and penetrating substances such as PCA, glycerol, propylene glycol monoethyl ether, carbonates, hydrogencarbonates, guanidines, ureas, and primary, secondary, and tertiary phosphates,
- opacifiers such as latex or styrene/acrylamide copolymers,
- pearlizing agents such as ethylene glycol mono- and distearate or PEG-3 distearate,
- direct dyes, and
- propellants such as propane-butane mixtures, $N_2O$, dimethyl ether, $CO_2$, and air.

Furthermore, agents (a), (b), and/or (c) according to the invention can include further active substances, auxiliary substances, and additives, such as non-ionic polymers such as vinylpyrrolidinone/vinyl acrylate copolymers, polyvinylpyrrolidinone, vinylpyrrolidinone/vinyl acetate copolymers, polyethylene glycols, and polysiloxanes; additional silicones such as volatile or non-volatile, straight-chain, branched, or cyclic, crosslinked or uncrosslinked polyalkylsiloxanes (such as dimethicone or cyclomethicone), polyarylsiloxanes, and/or polyalkylarylsiloxanes, in particular polysiloxanes having organofunctional groups, such as substituted or unsubstituted amines (amodimethicone), carboxyl, alkoxy, and/or hydroxyl groups (dimethicone copolyols), linear polysiloxane (A)/polyoxyalkylene (B) block copolymers, graft silicone polymers; cationic polymers such as quaternized cellulose ethers, polysiloxanes having quaternary groups, dimethyldiallylammonium chloride polymers, acrylamide/dimethyldiallylammonium chloride copolymers, dimethylamino ethylmethacrylate/vinylpyrrolidinone copolymers quaternized with diethyl sulfate, vinylpyrrolidinone/imidazolinium methochloride copolymers, and quaternized polyvinyl alcohol; zwitterionic and amphoteric polymers; anionic polymers such as polyacrylic acids or crosslinked polyacrylic acids; structurants such as glucose, hair-conditioning compounds such as phospholipids, for example lecithin and cephalins; perfume oils, dimethyl isosorbide and cyclodextrins; fiber-structure-improving active substances, in particular mono-, di-, and oligosaccharides such as glucose, galactose, fructose, fruit sugar, and lactose; dyes for tinting the agent; anti-dandruff active substances such as piroctone olamine, Zinc Omadine, and climbazole; amino acids and oligopeptides; animal- and/or plant-based protein hydrolysates, including in the form of their fatty acid condensation products or possibly anionically or cationically modified derivatives; plant oils; light stabilizers and UV blockers; active substances such as panthenol, pantothenic acid, pantolactone, allantoin, pyrrolidinone carboxylic acids and salts thereof, and bisabolol; polyphenols, in particular hydroxycinnamic acids, 6,7-dihydroxycumarins, hydroxybenzoic acids, catechins, tannins, leucoanthocyanidins, anthocyanidins, flavanones, flavones, and flavonols; ceramides or pseudo-ceramides; vitamins, provitamins, and vitamin precursors; plant extracts; fats and waxes such as fatty alcohols, beeswax, montan wax, and paraffins; swelling and penetrating substances such as glycerol, propylene glycol monoethyl ether, carbonates, hydrogencarbonates, guanidines, ureas, and primary, secondary, and tertiary phosphates; opacifiers such as latex, styrene/PVP copolymers, and styrene/acrylamide copolymers; pearlizing agents such as ethylene glycol mono- and distearate and PEG-3 distearate; pigments; and propellants such as propane-butane mixtures, $N_2O$, dimethyl ether, $CO_2$, and air.

A person skilled in the art will make the selection of these further substances in accordance with the desired properties of the agents. With regard to further optional components and the used amounts of these components, the pertinent manuals known to a person skilled in the art are expressly referenced. The additional active substances and auxiliary substances are used in the agents according to the invention preferably in amounts of 0.0001 to 25 wt %, more particularly 0.0005 to 15 wt %, in each case, with respect to the total weight of the application mixture.

Decoloring of Dyed Keratin Fibers

The multi-component packaging unit according to the invention is a system comprising agents (a), (b), and (c) that is used to decolor previously dyed keratin fibers, more particularly human hair. The dyed keratin fibers are usually fibers that were previously dyed with conventional oxidation dyes and/or direct dyes known to a person skilled in the art.

The decoloring agents are suitable for removing colorings that were produced on the keratin fibers by means of oxidation dyes based on developer and coupler components. If the following compounds were used as developers, the colorings produced by means thereof can be removed well, effectively, and nearly without later post-darkening by using the decoloring agent: p-phenylenediamine, p-toluylenediamine, N,N-bis(β-hydroxyethyl)-p-phenylenediamine, 4-N,N-bis(β-hydroxyethyl)-amino-2-methylaniline, 2-(β-hydroxyethyl)-p-phenylenediamine, 2-(α,β-dihydroxyethyl)-p-phenylenediamine, 2-hydroxymethyl-p-phenylenediamine, bis(2-hydroxy-5-aminophenyl)-methane, p-aminophenol, 4-amino-3-methylphenol, 2,4,5,6-tetraaminopyrimidine, 4-hydroxy-2,5,6-triaminopyrimidine, 2-hydroxy-4,5,6-triaminopyrimidine, and/or 4,5-diamino-1-(β-hydroxyethyl)pyrazole.

If the following compounds were used as couplers, the colorings produced by means thereof likewise can be removed with very good decoloring results: m-phenylenediamine derivatives, naphthols, resorcinol and resorcinol derivatives, pyrazolones, and m-aminophenol derivatives. In particular, 1-naphthol, 1 5-, 2,7-, and 1,7-dihydroxynaphthalene, 5-amino-2-methylphenol, m-aminophenol, resorcinol, m-phenylenediamine, 1-phenyl-3-methylpyrazolone-5, 2,4-dichloro-3-aminophenol, 1,3-bis(2',4'-diaminophenoxy) propane, 2-chlororesorcinol, 4-chlororesorcinol, 2-chloro-6-methyl-3-aminophenol, 2-amino-3-hydroxypyridine, 2-methylresorcinol, 5-methylresorcinol, 2-methyl-4-chloro-5-aminophenol, and 2,6-dihydroxy-3,4-dimethylpyridine are suitable as coupler substances.

The substrate to be decolored can also have been dyed by means of direct dyes. In particular, nitrophenylenediamines, nitroaminophenols, azo dyes, anthraquinones, or indophenols are possible as direct dyes. For example, keratin fibers that have been dyed by means of the dyes known under the following international designations or trade names can be decolored by means of the multi-component packaging unit (kit of parts) according to the invention: compounds known as HC Yellow 2, HC Yellow 4, HC Yellow 5, HC Yellow 6, HC Yellow 12, Acid Yellow 1, Acid Yellow 10, Acid Yellow 23, Acid Yellow 36, HC Orange 1, Disperse Orange 3, Acid Orange 7, HC Red 1, HC Red 3, HC Red 10, HC Red 11, HC Red 13, Acid Red 33, Acid Red 52, HC Red BN, Pigment Red 57:1, HC Blue 2, HC Blue 12, Disperse Blue 3, Acid Blue 7, Acid Green 50, HC Violet 1, Disperse Violet 1, Disperse Violet 4, Acid Violet 43, Disperse Black 9, Acid Black 1, and Acid Black 52, and 1,4-diamino-2-nitrobenzene, 2-amino-4-nitrophenol, 1-4-bis(β-hydroxyethyl) amino-2-nitrobenzene, 3-nitro-4-(β-hydroxyethyl)aminophenol, 2-(2'-hydroxyethyl)amino-4, 6-dinitrophenol, 1-(2'-hydroxyethyl)amino-4-methyl-2-nitrobenzene, 1-amino-4-(2'-hydroxyethyl)amino-5-chloro-2-nitrobenzene, 4-amino-3-nitrophenol, 1-(2'-ureidoethyl)amino-4-nitrobenzene, 4-amino-2-nitrodiphenylamine-2'-carboxylic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid, and 2-chloro-6-ethylamino-1-hydroxy-4-nitrobenzene.

Furthermore, the substrates to be decolored can also be dyed by means of natural dyes occurring in nature, which are included, for example, in red henna, neutral henna, black henna, chamomile flower, sandalwood, black tea, alder buckthorn bark, sage, logwood, madder root, catechu, Christ's thorn jujube, and Alkanna root.

The decoloring agents according to the invention are intended to remove these colorings and therefore preferably include no dyes themselves, i.e., no oxidation dye intermediates of the developer type and of the coupler type and also no direct dyes.

In an additional preferred embodiment, a multi-component packaging unit (kit of parts) according to the invention is therefore characterized in that
the total amount of all dyes and oxidation dye intermediates included in agent (a) is at most 0.2 wt %, preferably at most 0.1 wt %, more preferably at most 0.05 wt %, and especially preferably at most 0.01 wt %, with respect to the total weight of agent (a),
the total amount of all dyes and oxidation dye intermediates included in agent (b) is at most 0.2 wt %, preferably at most 0.1 wt %, more preferably at most 0.05 wt %, and especially preferably at most 0.01 wt %, with respect to the total weight of agent (b), and
the total amount of all dyes and oxidation dye intermediates included in agent (c) is at most 0.2 wt %, preferably at most 0.1 wt %, more preferably at most 0.05 wt %, and especially preferably at most 0.01 wt %, with respect to the total weight of agent (c).

All amount specifications here refer to the total amount of all dyes, from the group of the direct dyes, oxidation dye intermediates, and natural dyes, that are included in the particular agent, which total amount is expressed in relation to the total weight of the particular agent.

Oxidants

The multi-component packaging unit according to the invention is used to reductively decolor dyed keratin fibers. Agents (a) and (b) together form the ready-to-use decoloring agent, which includes a reductant. For reasons of incompatibility and to avoid exothermic, uncontrollable reactions, agents (a) and (b) preferably do not include an oxidant.

The successive treatment of keratin fibers with reductants and oxidants can lead to severe hair damage. To keep the occurring damage to the keratin fibers as low as possible, it is therefore additionally preferred if post-treatment agent (c) also does not include an oxidant.

Here, the term "oxidants" is understood to mean, in particular, the oxidants that can also be used for oxidative decoloring, such as hydrogen peroxide and persulfates (potassium persulfate (alternatively potassium peroxydisulfate), sodium persulfate (sodium peroxydisulfate), and ammonium persulfate (alternatively ammonium peroxydisulfate)). Therefore, preferably none of agents (a), (b), and (c) include the aforementioned oxidants.

In an additional preferred embodiment, a multi-component packaging unit (kit of parts) according to the invention is therefore characterized in that
the total amount of all oxidants from the group of the peroxides and the persulfates included in agent (a) is at most 0.2 wt %, preferably at most 0.1 wt %, more preferably at most 0.05 wt %, and especially preferably at most 0.01 wt %, with respect to the total weight of agent (a),
the total amount of all oxidants from the group of the peroxides and the persulfates included in agent (b) is at most 0.2 wt %, preferably at most 0.1 wt %, more preferably at most 0.05 wt %, and especially preferably at most 0.01 wt %, with respect to the total weight of agent (b),
the total amount of all oxidants from the group of the peroxides and the persulfates included in agent (c) is at most 0.2 wt %, preferably at most 0.1 wt %, more preferably at most 0.05 wt %, and especially preferably at most 0.01 wt %, with respect to the total weight of agent (c).

Mixture Ratio of Agents (a) and (b)

As already described above, the ready-to-use decoloring agent is produced by mixing agents (a) and (b). In principle, agents (a) and (b) can be mixed in various mixture ratios, such as (a)/(b) of 20:1 to 1:20.

To ensure convenient mixing, it can be advantageous to use the two agents (a) and (b) in approximately equal amounts. Particularly if acidifying or alkalizing agents are used in concentrated form in agent (b), it can also be advantageous to use agent (a) in excess. However, if agent (a) is formulated water-free, it can also be advantageous, on the other hand, to use agent (b) in excess.

Agent (a) preferably includes the one or more reductants (a1) in a total amount of 5.0 to 100 wt %, preferably 45.0 to 100 wt %, more preferably 65.0 to 100 wt %, and especially preferably 85.0 to 100 wt %, with respect to the total weight of agent (a). Therefore, the one or more reductants can be relatively concentrated in agent (a).

Particularly if the reductants are used in high concentration ranges in agent (a), the use of an excess of agent (b) is desirable.

In an additional preferred embodiment, a multi-component packaging unit according to the invention is therefore characterized in that the amounts of agent (a) in container (A) and of agent (b) in container (B) are selected in such a way that, when the application mixture is produced—i.e., when agents (a) and (b) are mixed—the mixture ratio (a)/(b) is 1:5 to 1:30.

In an additional especially preferred embodiment, a multi-component packaging unit according to the invention is therefore characterized in that the amounts of agent (a) in container (A) and of agent (b) in container (B) are selected in such a way that, when the application mixture is produced—i.e., when agents (a) and (b) are mixed—the mixture ratio (a)/(b) is 1:8 to 1:20, extremely preferably 1:10 to 1:15.

For example, agent (a) can be completely transferred from container (A) into container (B), which already contains agent (b), to produce the mixture. In this case, the size of container (B) is selected in such a way that container (B) can hold the total amount of agents (a) and (b) and also permits mixing of the two agents (a) and (b), for example by shaking or stirring.

Analogously, the mixture can be produced also by completely transferring agent (b) from container (B) into container (A), which already contains agent (a). In this case, the size of container (A) should be selected in such a way that container (A) can hold the total amount of agents (a) and (b) and also permits mixing of the two agents (a) and (b), for example by shaking or stirring.

A further possibility for producing the application mixture is to completely transfer both agents (a) and (b) from containers (A) and (B) into a third vessel, which then permits the mixing of the two agents, for example by shaking or stirring.

Example: A multi-component packaging unit according to the invention includes
10 g of sodium dithionite, agent (a) in container (A) (i.e., the total content of reductant(s) (a1) in agent (a) is 100 wt % (minus slight contaminants in sodium dithionite)
100 g of agent (b) in container (B)

To produce the application mixture, agent (a) is completely transferred from container (A) into container (B). Agents (a) and (b) are then shaken or stirred with each other. The mixture ratio of the agents (a)/(b) is (10 g/100 g)=1:10.

Method

The previously described multi-component packaging units (kit of parts) according to the invention can be used in methods for reductive decoloring.

Therefore, a second subject matter of the present invention is a method for reductively decoloring dyed keratin fibers, more particularly human hair, comprising the following steps in the indicated order:
(I) producing a ready-to-use decoloring agent by mixing an agent (a), as it was defined in the description of the first subject matter, with an agent (b), as it was defined in the description of the first subject matter,
(II) applying the ready-to-use decoloring agent to keratin fibers,
(III) allowing the decoloring agent to act for a time period of 5 to 60 minutes, preferably 10 to 55 minutes, more preferably 20 to 50 minutes, and especially preferably 30 to 45 minutes,
(IV) rinsing the decoloring agent off of the keratin fibers,
(V) applying a cosmetic aqueous agent (c) to the keratin fibers, wherein agent (c) is an agent as defined in the description of the first subject matter of the invention,
(VI) allowing agent (c) to act for a time period of 30 seconds to 30 minutes, preferably 30 seconds to 20 minutes, more preferably 30 seconds to 10 minutes, and especially preferably 30 seconds to 5 minutes, and
(VII) rinsing agent (c) off of the keratin fibers.

Steps (I), (II), (III), and (IV) of the method constitute the decoloring process of the keratin fibers and are therefore performed one after the other in direct chronological sequence. In principle, there is no time limitation for the sequence of steps (IV) and (V). Thus, step (V) can occur hours, days, or, for example, also up to two weeks after the conclusion of step (IV).

However, the method should prevent redarkening or reoxidation, which can occur by the action of atmospheric oxygen on the decolored keratin fibers. To prevent this reoxidation effectively, the post-treatment should occur before the atmospheric oxygen can act on the reduced keratin fibers over an excessively long time period. For this reason, the post-treatment should occur immediately following the decoloring (i.e., immediately after step (IV) has been concluded), to the extent possible. For this reason, it is preferred if a time period of at most 12 hours, preferably at most 6 hours, more preferably at most 1 hour, and especially preferably at most 30 minutes, lies between the conclusion of step (IV) and the start of step (V).

A preferred method according to the invention is therefore characterized in that a time period of at most 12 hours, preferably at most 6 hours, more preferably at most 1 hour, and especially preferably at most 30 minutes, lies between steps (IV) and (V).

The use of the post-treatment agent can also be repeated several times, for example if agent (c) is a shampoo that is used regularly after the decoloring. If the post-treatment, i.e., the performance of steps (V) to (VII), is repeated, it is possible to suppress the reoxidation for a particularly long time period.

An especially preferred method according to the invention is therefore characterized in that the following steps are performed in the indicated order following step (VII):
(VIII) applying a cosmetic aqueous agent (c) to the keratin fibers, wherein agent (c) is an agent as defined in the description of the first subject matter of the invention,
(IX) allowing agent (c) to act for a time period of 30 seconds to 30 minutes, preferably 30 seconds to 20 minutes, more preferably 30 seconds to 10 minutes, and especially preferably 30 seconds to 5 minutes, and
(X) rinsing agent (c) off of the keratin fibers.

Steps (VIII) to (X) constitute one repetition of the post-treatment with agent (c); this post-treatment occurs following step (VII). In principle, there is no time limitation for the sequence of steps (VII) and (VIII). However, for the sake of convenience for the user, it is preferred if the post-treatment with agent (c) is performed as part of the typical hair washing performed by the user. If the user normally washes the user's hair every one to two days, for example, post-treatment agent (c) should be used for this hair washing. Therefore, it is preferred if a time interval of 12 to 48 hours, preferably 24 to 36 hours, lies between steps (VII) and (VIII).

The method according to the invention is effective particularly for keratin fibers that have been dyed by means of certain oxidation dye intermediates.

Good results were achieved especially if the decoloring method was applied to keratin fibers that were dyed by means of one or more oxidation dye intermediates from the group comprising p-phenylenediamine, p-toluylenediamine, N,N-bis(β-hydroxyethyl)-p-phenylenediamine, 2-(β-hydroxyethyl)-p-phenylenediamine, and/or 2-(methoxymethyl)-p-phenylenediamine.

A preferred method according to the invention is therefore furthermore characterized in that the ready-to-use decoloring agent is applied to keratin fibers that have been dyed by means of at least one oxidation dye intermediate from the group comprising p-phenylenediamine, p-toluylenediamine, N,N-bis(β-hydroxyethyl)-p-phenylenediamine, 2-(β-hydroxyethyl)-p-phenylenediamine, and/or 2-(methoxymethyl)-p-phenylenediamine.

The statements made with regard to the agents according to the invention apply, mutatis mutandis, to additional preferred embodiments of the method according to the invention.

EXAMPLES 1.1. Coloring

The following formulations were produced (all specifications in wt %):

Dyeing Cream (F1)

| Raw substance | wt % |
| --- | --- |
| Cetearyl alcohol | 8.5 |
| C12-C18 fatty alcohols | 3.0 |
| Ceteareth-20 | 0.5 |
| Ceteareth-12 | 0.5 |
| Plantacare 1200 UP (lauryl glucosides, 50-53% aqueous solution) | 2.0 |
| Sodium laureth-6 carboxylate (21% aqueous solution) | 10.0 |
| Sodium myreth sulfate (68-73% aqueous solution) | 2.8 |
| Sodium acrylate/trimethylammoniopropylacrylamide chloride copolymer (19-21% aqueous solution) | 3.8 |
| Potassium hydroxide | 0.83 |
| p-Toluylenediamine sulfate | 2.25 |
| m-Aminophenol | 0.075 |
| 2-Amino-3-hydroxypyridine | 0.12 |
| Resorcinol | 0.62 |
| 4-Chlororesorcinol | 0.26 |
| 3-Amino-2-methylamino-6-methoxypyridine | 0.04 |
| 1,3-Bis(2,4-diaminophenoxy)propane tetrahydrochloride | 0.05 |
| Ammonium sulfate | 0.1 |
| Sodium sulfite | 0.4 |
| Ascorbic acid | 0.1 |

-continued

| Raw substance | wt % |
|---|---|
| 1-Hydroxyethane-1,1-diphosphonic acid (60% aqueous solution) | 0.2 |
| Ammonia (25% aqueous solution) | 7.2 |
| Water | Ad 100 |

Oxidant (Ox)

| Raw substance | wt % |
|---|---|
| Sodium benzoate | 0.04 |
| Dipicolinic acid | 0.1 |
| Disodium pyrophosphate | 0.1 |
| Potassium hydroxide | 0.09 |
| 1,2-Propylene glycol | 1.0 |
| 1-Hydroxyethane-1,1-diphosphonic acid (60% aqueous solution) | 0.25 |
| Paraffinum liquidum | 0.30 |
| Steartrimonium chloride | 0.39 |
| Cetearyl alcohol | 3.4 |
| Ceteareth-20 | 1.0 |
| Hydrogen peroxide (50% aqueous solution) | 12.0 |

Dyeing cream (F1) and oxidant (Ox) were mixed in an amount ratio of 1:1 and applied to hair strands (Kerling European natural hair, white). The weight ratio of application mixture to hair was 4:1, and the exposure time was 30 minutes at a temperature of 32 degrees Celsius. Then the strands were rinsed with water, dried, and allowed to rest at room temperature for at least 24 hours. The strands were dyed in a dark-brown shade of color.

1.2. Decoloring

The following decoloring agents were produced:

Agent (a)

|  | (a1) | (a2) |
|---|---|---|
| Sodium dithionite | 5.0 g | — |
| Formamidine sulfinic acid | — | 5.0 g |

Agent (b)

|  | (b1) | (b2) |
|---|---|---|
| Cetearyl alcohol | 2.9 g | 2.9 g |
| PEG-40 Castor Oil | 0.55 g | 0.55 g |
| Sodium cetearyl sulfate | 0.28 g | 0.28 g |
| Hydroxyethane-1,1-diphosphonic acid (1-etidronic acid) | 0.24 g | — |
| Monoethanolamine | — | 0.95 |
| Water (distilled) | Ad 95 g | Ad 95 g |

Agents (a) and (b) were mixed (5 g of agent (a1) were mixed with 95 g of agent (b1); analogously, 5 g of agent (a2) were mixed with 95 g of agent (b2)). These ready-to-use decoloring agents were each applied to the hair colored under point 1.1 and allowed to act for 30 minutes at a temperature of 30° C. Thereafter, the strands were rinsed with water for 20 seconds and dried in a warm air flow. Then the hair strands were colorimetrically measured. The L value was determined in each case as a measure of the lightness of a strand.

Agent (c)

| Agent (c) | Comparison | (c1) | (c2) |
|---|---|---|---|
| Maleic acid | — | 5.0 | 2.5 |
| Citric acid | — | — | 2.5 |
| Cetearyl alcohol | 2.9 g | 2.9 g | 2.9 g |
| PEG-40 Castor Oil | 0.55 g | 0.55 g | 0.55 g |
| Sodium cetearyl sulfate | 0.28 g | 0.28 g | 0.28 g |
| Water | Ad 100 | Ad 100 | Ad 100 |

Directly following the colorimetric measurement, the decolored strands were treated with post-treatment agent (c) (or with the comparison) for 5 minutes, rinsed with water for 20 seconds, and dried in a warm air flow. Then the hair strands were colorimetrically measured again and the L value was determined.

The decoloring result was evaluated by determining the $\Delta L$ value.

$\Delta L = L$(after the decoloring)$- L$(before the decoloring)

The higher the $\Delta L$ value is, the better the dyed hair strands were decolored.

|  | Comparison | (c1) | (c2) |
|---|---|---|---|
| Decoloring with (a1) + (b1) (sodium dithionite) | | | |
| $\Delta L$ value | 9.6 | 20.8 | 23.3 |
| Decoloring with (a2) + (b2) (formamidine sulfinic acid) | | | |
| $\Delta L$ value | 18.5 | 24.8 | 27.7 |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A multi-component packaging unit (kit of parts) for reductively decoloring dyed keratin fibers, which includes
   (I) a container (A) containing a cosmetic agent (a) comprising a reductant of formamidine sulfinic acid and/or physiologically acceptable salts thereof,
   (II) a container (B) containing a cosmetic agent (b) comprising water and monoethanolamine, wherein agent (b) has a pH of 7 to 12,
   (III) a container (C) containing an aqueous, cosmetic agent (c) comprising 1.0 to 5.0 wt % maleic acid and 1.0 to 5.0 wt % citric acid,
      wherein agent (c) has a pH of 0.5 to 4.0.

2. The multi-component packaging unit (kit of parts) according to claim 1, wherein agent (a) in container (A) further includes
   (a1) one or more reductants selected from the group consisting of sodium dithionite, zinc dithionite, potassium dithionite, [bis(sulfinomethyl)amino]methanesulfinic acid, and physiologically acceptable salts of the aforementioned acids.

3. The multi-component packaging unit (kit of parts) according claim 1, wherein agent (a) in container (A) includes—with respect to the total weight of agent (a)—
(a1) the formamidine sulfinic acid in a total amount of 5.0 to 100 wt %.

4. The multi-component packaging unit (kit of parts) according to claim 1, wherein
agent (a) in container (A) further includes one or more of sodium dithionite, zinc dithionite, and potassium dithionite.

5. The multi-component packaging unit (kit of parts) according to claim 4, wherein agent (b) in container (B) further comprises an acid selected from the group consisting of citric acid, tartaric acid, malic acid, lactic acid, acetic acid, hydroxyethane-1,1-diphosphonic acid, methanesulfonic acid, benzoic acid, oxaloacetic acid, hydrochloric acid, sulfuric acid, phosphoric acid, malonic acid, and oxalic acid.

6. The multi-component packaging unit (kit of parts) according to claim 1, wherein
agent (b) in container (B) further includes
(b2') one or more alkalizing agents selected from the group consisting of ammonia, 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, and 2-amino-2-methylpropan-1,3-diol.

7. The multi-component packaging unit (kit of parts) according to claim 1, wherein agent (c) in container (C) further includes
(c1) one or more compounds of formula (I) different from the maleic acid and citric acid,

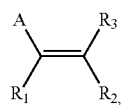

wherein
R1, R2, R3 represent, independently of each other, a hydrogen atom, a —COOM group, or a $C_1$-$C_{10}$ alkyl group,
M represents a hydrogen atom, an ammonium group $(NH_4)^+$, or an equivalent of a monovalent or multivalent alkali-metal or alkaline-earth-metal cation,
A represents a —COOM group or a —$(CH_2)_n$—COOM group, and
n represents an integer from 1 to 10.

8. The multi-component packaging unit (kit of parts) according to claim 7, wherein
one or more compounds of formula (I) is selected from the group consisting of fumaric acid, itaconic acid, oleic acid, palmitoleic acid, and/or physiologically acceptable salts thereof.

9. The multi-component packaging unit (kit of parts) according to claim 1, wherein agent (c) in container (C) further includes
(c2) one or more acids selected from the group consisting of tartaric acid, malic acid, lactic acid, acetic acid, hydroxyethane-1,1-diphosphonic acid, methanesulfonic acid, benzoic acid, hydrochloric acid, sulfuric acid, phosphoric acid, malonic acid, oxaloacetic acid, and oxalic acid.

10. The multi-component packaging unit (kit of parts) according to claim 7, wherein agent (c) in container (C) further includes
one or more compounds (c1) of formula (I) and further includes one or more acids of group (c2) in a weight ratio (c1)/(c2) of 10:1 to 1:10, wherein the acids of group (c2) are selected from the group consisting of tartaric acid, malic acid, lactic acid, acetic acid, hydroxyethane-1,1-diphosphonic acid, methanesulfonic acid, benzoic acid, hydrochloric acid, sulfuric acid, phosphoric acid, malonic acid, oxaloacetic acid, and oxalic acid.

11. The multi-component packaging unit (kit of parts) according to claim 1, wherein
agent (a) in container (A) is a water-free agent, and
agent (c) in container (C) has a pH value of 0.5 to 4.0.

12. The multi-component packaging unit (kit of parts) according to claim 1, wherein agent (c) further includes fumaric acid.

13. The multi-component packaging unit (kit of parts) according to claim 1, wherein agent (a1) consists of the formamidine sulfinic acid.

14. The multi-component packaging unit (kit of parts) according to claim 1, wherein cosmetic agent (b) comprises the water, the monoethanolamine, cetearyl alcohol, ethoxylated castor oil, hydrogenated castor oil, and sodium cetearyl sulfate.

15. The multi-component packaging unit (kit of parts) according to claim 14, wherein cosmetic agent (c) comprises the maleic acid, the citric acid, cetearyl alcohol, ethoxylated castor oil, hydrogenated castor oil, water, and sodium cetearyl sulfate.

16. The multi-component packaging unit (kit of parts) according to claim 15 wherein cosmetic agent (a1) consists of the formamidine sulfinic acid.

17. The multi-component packaging unit (kit of parts) according to claim 1
wherein the reductant is selected from the group consisting of formamidine sulfinic acid, physiologically acceptable salts thereof, and combinations thereof,
wherein the cosmetic agent (c) comprises maleic acid and citric acid in a weight ratio of 3:2 to 2:3.

18. A method for reductively decoloring dyed keratin fibers, including the following steps in the indicated order:
(I) producing a ready-to-use decoloring agent by mixing agent (a) defined in claim 1, with agent (b),
(II) applying the ready-to-use decoloring agent to keratin fibers,
(III) allowing the decoloring agent to act for a time period of 5 to 60 minutes,
(IV) rinsing the decoloring agent off of the keratin fibers,
(V) applying cosmetic aqueous agent (c) to the keratin fibers,
(VI) allowing agent (c) to act for a time period of 30 seconds to 30 minutes, and
(VII) rinsing agent (c) off of the keratin fibers.

19. The method according to claim 18, further including the following steps, which are performed in the indicated order following step (VII):
(VIII) applying cosmetic aqueous agent (c) to the keratin fiber,
(IX) allowing agent (c) to act for a time period of 30 seconds to 30 minutes, and
(X) rinsing agent (c) off of the keratin fibers.

20. The method according to claim 1, wherein the ready-to-use decoloring agent is applied to keratin fibers that have been previously dyed by means of at least one oxidation dye intermediate from the group comprising p-phenylenediamine, p-toluylenediamine, N,N-bis(β-hydroxyethyl)-p-phenylenediamine, 2-(β-hydroxyethyl)-p-phenylenediamine, and/or 2-(methoxymethyl)-p-phenylenediamine.

* * * * *